(12) United States Patent
Hillukka et al.

(10) Patent No.: US 11,957,921 B2
(45) Date of Patent: Apr. 16, 2024

(54) CATHETER-BASED DELIVERY SYSTEM FOR DELIVERING A LEADLESS PACEMAKER AND EMPLOYING A LOCKING HUB

(71) Applicant: PACESETTER, INC., Sylmar, CA (US)

(72) Inventors: Brett Hillukka, Hanover, MN (US); Thomas B. Eby, Mountain View, CA (US); Christopher Alan Hubbard, Woodridge, MN (US); Bernhard Arnar, Minnetrista, MN (US); Bradley Knippel, Lino Lakes, MN (US); Jeremiah Blue, Andover, MN (US); Jennifer Heisel, Princeton, MN (US); Rebecca Stufft, Plymouth, MN (US); Adam Weber, Minnetonka, MN (US)

(73) Assignee: PACESETTER, INC., Sylmar, CA (US)

( * ) Notice: Subject to any disclaimer, the term of this patent is extended or adjusted under 35 U.S.C. 154(b) by 439 days.

(21) Appl. No.: 17/160,210

(22) Filed: Jan. 27, 2021

(65) Prior Publication Data

US 2021/0178169 A1 Jun. 17, 2021

Related U.S. Application Data

(62) Division of application No. 15/942,105, filed on Mar. 30, 2018, now Pat. No. 10,960,217.

(Continued)

(51) Int. Cl.
*A61N 1/375* (2006.01)
*A61B 17/34* (2006.01)
(Continued)

(52) U.S. Cl.
CPC ........ *A61N 1/3756* (2013.01); *A61B 17/3468* (2013.01); *A61M 25/0097* (2013.01);
(Continued)

(58) Field of Classification Search
CPC ............ A61B 19/201; A61B 2019/208; A61B 17/3468; A61N 1/375; A61N 1/3756; A61N 1/05
See application file for complete search history.

(56) References Cited

U.S. PATENT DOCUMENTS 3,123,484 A 3/1964 Pokras et al.
3,148,072 A 9/1964 West et al.
(Continued)

FOREIGN PATENT DOCUMENTS

WO 2007/047681 A2 4/2007

OTHER PUBLICATIONS

U.S. Appl. No. 62/408,494, filed Oct. 14, 2016, 31 pages.
U.S. Appl. No. 62/434,537, filed Dec. 15, 2016, 32 pages.
U.S. Appl. No. 12/698,969, filed Feb. 2, 2010, 26 pages.

*Primary Examiner* — Vi X Nguyen
(74) *Attorney, Agent, or Firm* — WOMBLE BOND DICKINSON (US) LLP

(57) ABSTRACT

Disclosed herein is a delivery system for delivering a leadless pacemaker. The delivery system may include a catheter, which may be a guide catheter. The catheter includes a distal end, a proximal end opposite the distal end, a lumen extending between the distal end and the proximal end, and a locking hub operably coupled to the proximal end. The locking hub includes a lumen segment of the lumen. In one implementation, self-biasing of the lumen segment places the lumen segment out of alignment with a rest of the lumen. Deflecting the lumen segment against the self-biasing of the lumen segment places the lumen segment in coaxial alignment with the rest of the lumen. In another (Continued)

implementation, self-biasing of the lumen segment reduces an inner diameter of the lumen segment and actuation of the locking hub expands the inner diameter.

7 Claims, 33 Drawing Sheets

Related U.S. Application Data

(60) Provisional application No. 62/636,063, filed on Feb. 27, 2018, provisional application No. 62/503,888, filed on May 9, 2017, provisional application No. 62/480,087, filed on Mar. 31, 2017.

(51) Int. Cl.
*A61M 25/00* (2006.01)
*A61N 1/05* (2006.01)
*A61N 1/362* (2006.01)
*A61N 1/378* (2006.01)

(52) U.S. Cl.
CPC .... *A61N 1/0573* (2013.01); *A61N 2001/0578* (2013.01); *A61N 1/362* (2013.01); *A61N 1/37512* (2017.08); *A61N 1/37518* (2017.08); *A61N 1/3787* (2013.01)

(56) References Cited

U.S. PATENT DOCUMENTS

| | | | |
|---|---|---|---|
| 3,338,726 A | 8/1967 | Berzins | |
| 3,719,508 A | 3/1973 | Gulla et al. | |
| 3,745,039 A | 7/1973 | Feldstein | |
| 3,754,939 A | 8/1973 | Pearlstein et al. | |
| 3,915,717 A | 10/1975 | Feldstein et al. | |
| 4,152,164 A | 5/1979 | Gulla et al. | |
| 5,125,915 A | 6/1992 | Berry et al. | |
| 5,849,011 A | 12/1998 | Jones et al. | |
| 6,143,059 A | 11/2000 | Tangi et al. | |
| 6,254,571 B1 * | 7/2001 | Hart | A61B 17/221 604/107 |
| 6,281,157 B1 | 8/2001 | Tangi et al. | |
| 6,292,695 B1 * | 9/2001 | Webster, Jr. | A61N 1/0563 607/148 |
| 6,524,642 B1 | 2/2003 | Leibman et al. | |
| 7,740,608 B2 | 6/2010 | Lampropoulos et al. | |
| 7,846,503 B2 | 12/2010 | Stark et al. | |
| 7,937,148 B2 | 5/2011 | Jacobson | |
| 7,945,333 B2 | 5/2011 | Jacobson | |
| 8,010,209 B2 | 8/2011 | Jacobson | |
| 8,352,025 B2 | 1/2013 | Jacobson | |
| 8,457,742 B2 | 6/2013 | Jacobson | |
| 8,457,745 B1 | 6/2013 | Jacobson | |
| 8,527,068 B2 | 9/2013 | Ostroff | |
| 8,615,310 B2 | 12/2013 | Kahairkhahan et al. | |
| 8,958,892 B2 | 2/2015 | Kahairkhahan et al. | |
| 9,205,225 B2 | 12/2015 | Kahairkhahan et al. | |
| 9,216,298 B2 | 12/2015 | Jacobson | |
| 9,320,590 B2 | 4/2016 | Zaver et al. | |
| 9,358,400 B2 | 6/2016 | Jacobson | |
| 9,462,699 B2 | 10/2016 | Radi et al. | |
| 2007/0083189 A1 | 4/2007 | Lampropoulos et al. | |
| 2007/0088394 A1 | 4/2007 | Jacobson | |
| 2007/0088396 A1 | 4/2007 | Jacobson | |
| 2007/0088397 A1 | 4/2007 | Jacobson | |
| 2007/0088398 A1 | 4/2007 | Jacobson | |
| 2007/0088400 A1 | 4/2007 | Jacobson | |
| 2007/0088405 A1 | 4/2007 | Jacobson | |
| 2007/0088418 A1 | 4/2007 | Jacobson | |
| 2016/0121007 A1 | 5/2016 | Dayton | |

\* cited by examiner

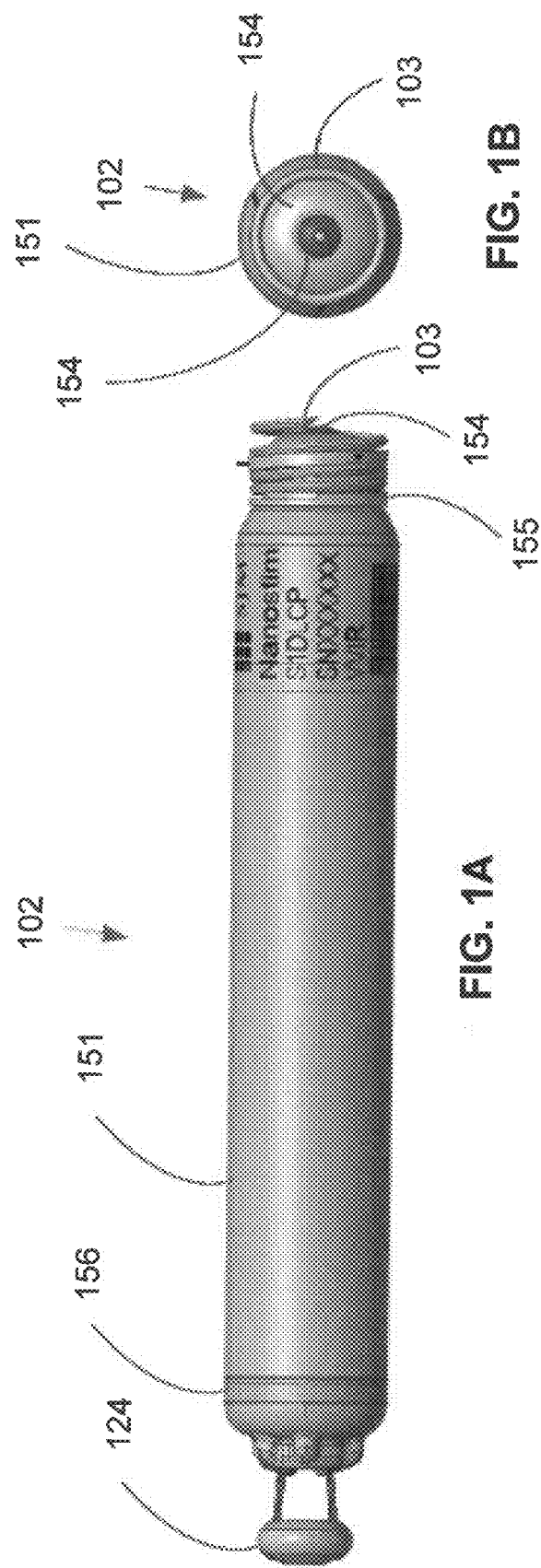

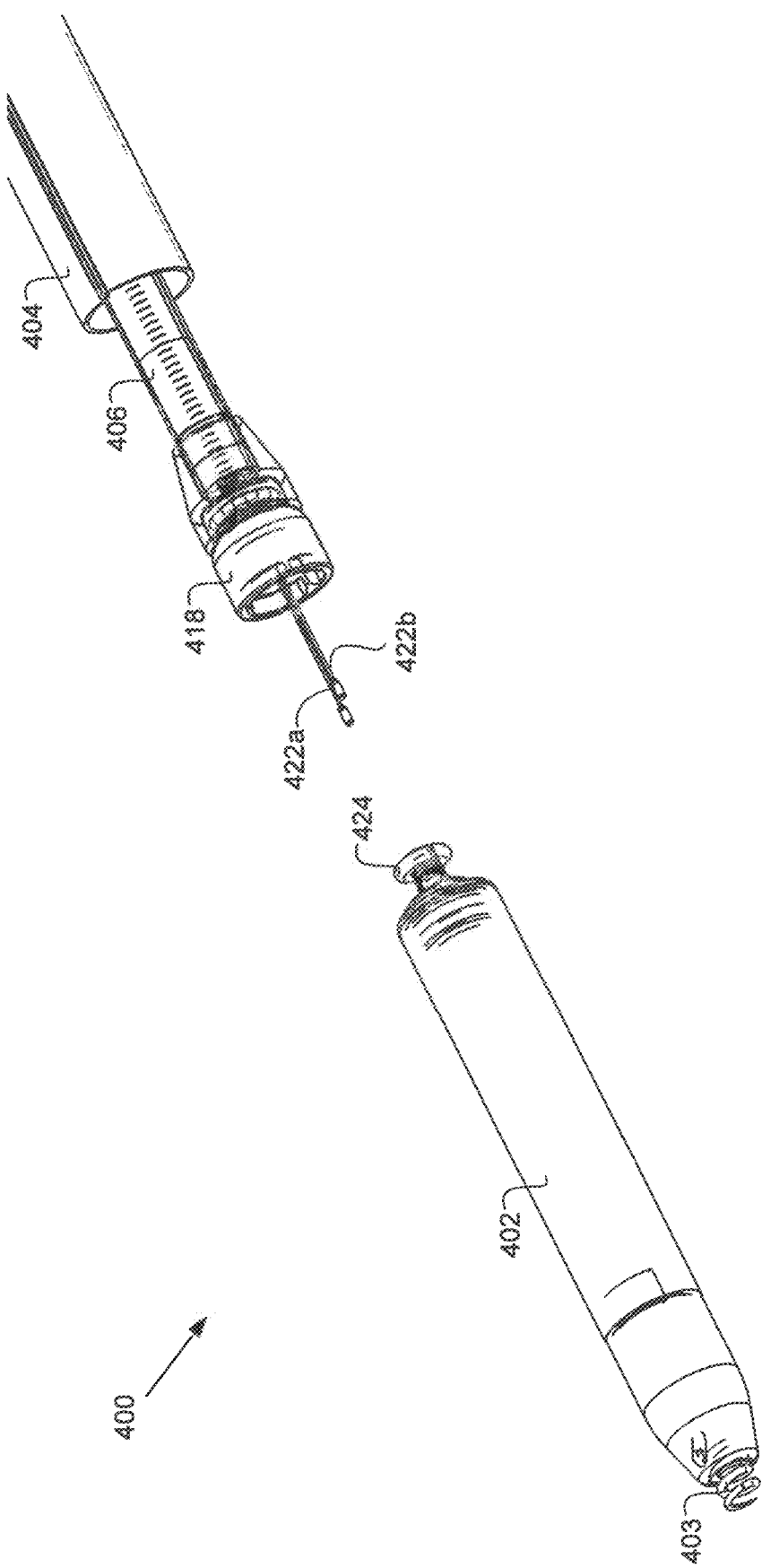

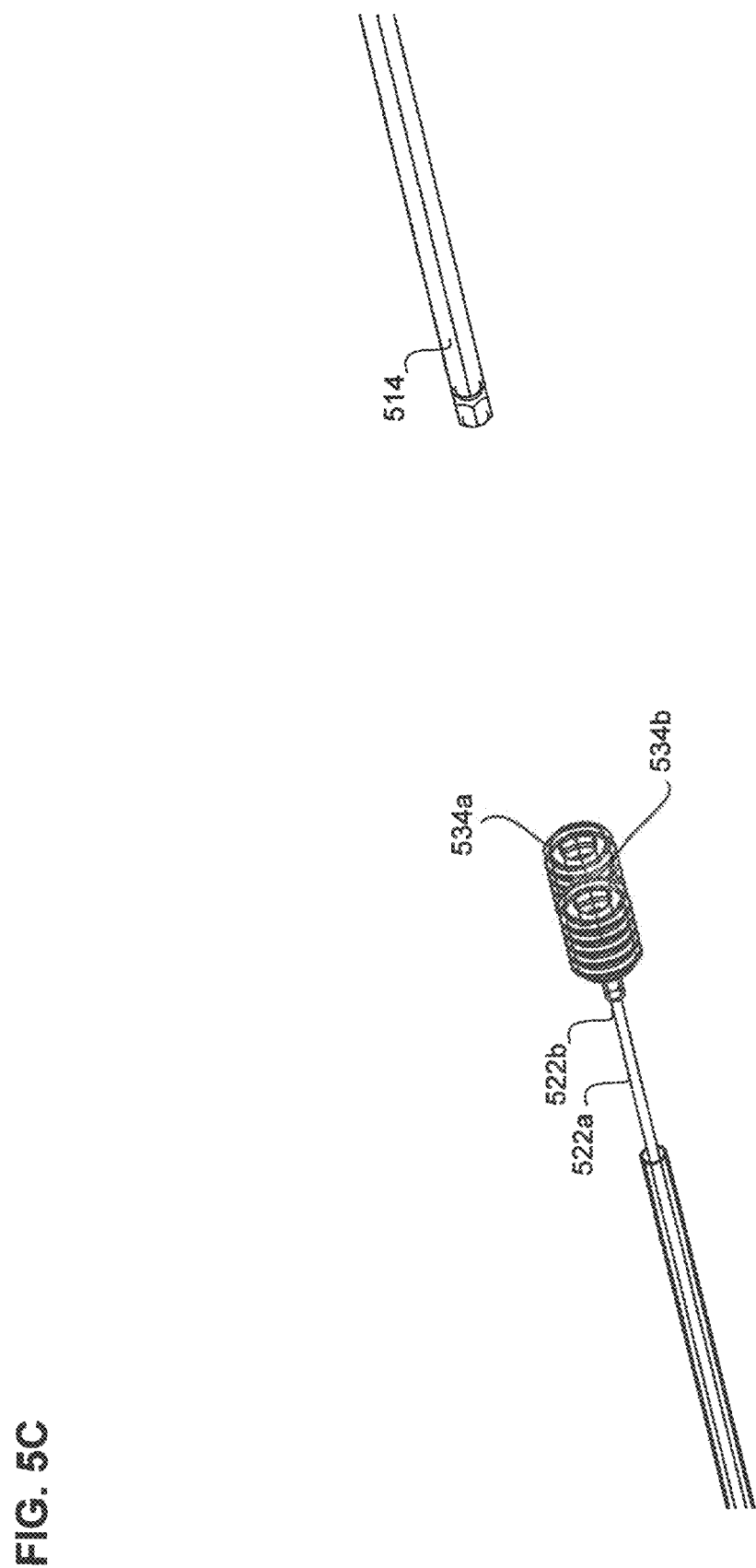

CATHETER-BASED DELIVERY SYSTEM FOR DELIVERING A LEADLESS PACEMAKER AND EMPLOYING A LOCKING HUB

CROSS-REFERENCE TO RELATED APPLICATION

This application is a divisional under 35 U.S.C. § 120 of U.S. patent application Ser. No. 15/942,105, filed Mar. 30, 2018, titled "Catheter-Based Delivery System For Delivering A Leadless Pacemaker And Employing A Locking Hub," and claims priority under 35 U.S.C. § 119(e) from U.S. Patent Application No. 62/480,087, filed Mar. 31, 2017, titled "Catheter-Based Delivery System For Delivering A Leadless Pacemaker And Employing A Locking Hub," U.S. Patent Application No. 62/503,888, filed May 9, 2017, titled "Catheter-Based Delivery System For Delivering A Leadless Pacemaker And Employing A Locking Hub" and U.S. Patent Application No. 62/636,063, filed Feb. 27, 2018, titled "Catheter-Based Delivery System For Delivering A Leadless Pacemaker And Employing A Locking Hub," and the entire contents of those applications are incorporated herein by reference for all purposes.

INCORPORATION BY REFERENCE

All publications and patent applications mentioned in this specification are herein incorporated by reference to the same extent as if each individual publication or patent application was specifically and individually indicated to be incorporated by reference.

FIELD

The present disclosure relates to leadless cardiac pacemakers and related delivery systems and methods. More specifically, the present disclosure relates to devices and methods for delivering a leadless cardiac pacemaker via a catheter-based delivery system.

BACKGROUND

Cardiac pacing by an artificial pacemaker provides an electrical stimulation of the heart when its own natural pacemaker and/or conduction system fails to provide synchronized atrial and ventricular contractions at rates and intervals sufficient for a patient's health. Such antibradycardial pacing provides relief from symptoms and even life support for hundreds of thousands of patients. Cardiac pacing may also provide electrical overdrive stimulation to suppress or convert tachyarrhythmias, again supplying relief from symptoms and preventing or terminating arrhythmias that could lead to sudden cardiac death.

Cardiac pacing by currently available or conventional pacemakers is usually performed by a pulse generator implanted subcutaneously or sub-muscularly in or near a patient's pectoral region. Pulse generator parameters are usually interrogated and modified by a programming device outside the body, via a loosely-coupled transformer with one inductor within the body and another outside, or via electromagnetic radiation with one antenna within the body and another outside. The generator usually connects to the proximal end of one or more implanted leads, the distal end of which contains one or more electrodes for positioning adjacent to the inside or outside wall of a cardiac chamber. The leads have an insulated electrical conductor or conductors for connecting the pulse generator to electrodes in the heart. Such electrode leads typically have lengths of 50 to 70 centimeters.

Although more than one hundred thousand conventional cardiac pacing systems are implanted annually, various well-known difficulties exist. For example, a pulse generator, when located subcutaneously, presents a bulge in the skin that patients can find unsightly, unpleasant, or irritating, and which patients can subconsciously or obsessively manipulate or "twiddle". Even without persistent manipulation, subcutaneous pulse generators can exhibit erosion, extrusion, infection, disconnection, insulation damage, or conductor breakage at the wire leads. Although sub-muscular or abdominal placement can address some concerns, such placement involves a more difficult surgical procedure for implantation and adjustment, which can prolong patient recovery.

A conventional pulse generator, whether pectoral or abdominal, has an interface for connection to and disconnection from the electrode leads that carry signals to and from the heart. Usually at least one male connector molding has at least one terminal pin at the proximal end of the electrode lead. The male connector mates with a corresponding female connector molding and terminal block within the connector molding at the pulse generator. Usually a setscrew is threaded in at least one terminal block per electrode lead to secure the connection electrically and mechanically. One or more O-rings usually are also supplied to help maintain electrical isolation between the connector moldings. A setscrew cap or slotted cover is typically included to provide electrical insulation of the setscrew. This briefly described complex connection between connectors and leads provides multiple opportunities for malfunction.

Other problematic aspects of conventional pacemakers relate to the separately implanted pulse generator and the pacing leads. By way of another example, the pacing leads, in particular, can become a site of infection and morbidity. Many of the issues associated with conventional pacemakers are resolved by the development of a self-contained and self-sustainable pacemaker, or so-called leadless pacemaker, as described in the applications cited below.

Similar to active fixation implantable leads used with conventional pulse generators, leadless pacemakers are typically fixed to an intracardial implant site by an actively engaging mechanism such as a screw or helical member that screws into the myocardium.

Leadless pacemakers are typically delivered to an intracardial implant site via a delivery system including catheters, sheaths and/or introducers. It is a complicated and delicate task to introduce a leadless pacemaker into the venous system and then navigate the leadless pacemaker through and past delicate tissues and anatomical structures to the implantation site. To achieve this task, the sheaths, catheters and introducers are often manipulated relative to each other, and such manipulation needs to be precise. There is a need in the art for systems and methods that facilitate this precision.

SUMMARY OF THE DISCLOSURE

Disclosed herein is a delivery system for delivering a leadless pacemaker. In one embodiment the delivery system includes a catheter including a distal end, a proximal end opposite the distal end, a lumen extending between the proximal end and the distal end and shaped to receive an elongate body, and a locking hub operably coupled to the proximal end. The locking hub includes a lumen segment of the lumen. The locking hub biases the lumen segment such that the lumen segment provides a first resistance to movement of the elongate body within the lumen when the elongate body is received by the catheter. Actuating the locking hub causes the lumen segment to provide a second resistance to movement of the elongate body within the lumen when the elongate body is received by the catheter, the second resistance being less than the first resistance.

In one implementation, the locking hub includes one or more buttons and actuating the locking hub includes depressing the one or more buttons. The one or more buttons are disposed about a longitudinal axis of the catheter such that depressing the one or more buttons causes the one or more buttons to displace toward the longitudinal axis.

In another implementation, the locking hub includes a biasing element for providing the first resistance. The biasing element may include one or more of a helical spring, a leaf spring, a biasing arm, or a resilient elastomeric member.

In yet another implementation, the locking hub biases the lumen segment by reducing a diameter of the lumen segment to a first diameter. In such implementations, actuating the locking hub may change the diameter of the lumen segment to a second diameter, the second diameter being greater than the first diameter.

In another implementation, the locking hub biases the lumen segment to be out of alignment with a rest of the lumen. In one such implementation, actuating the locking hub places the lumen segment in coaxial alignment with the rest of the lumen.

In another embodiment, a delivery system for delivering a leadless pacemaker is provided. The delivery system includes a catheter including a distal end, a proximal end opposite the distal end, a lumen extending between the proximal end and the distal end, and a locking hub operably coupled to the proximal end. The locking hub includes a movable member that further includes a lumen segment of the lumen. The movable member is biased in a first direction transverse relative to a longitudinal axis of the lumen such that the lumen segment is biased out of alignment with a rest of the lumen. Actuating the locking hub translates the movable member in a second transverse direction opposite the first transverse direction to coaxially align the lumen segment with the rest of the lumen.

In one implementation, wherein the locking hub includes one or more buttons and actuating the locking hub includes depressing the one or more buttons. In one such implementation, depressing the one or more buttons causes translation of the one or more buttons in a transverse direction relative to the longitudinal axis of the lumen.

In another implementation, the locking hub comprises a biasing element configured to bias the movable member in the first direction. Such a biasing element may include, without limitation, one or more of a helical spring, a leaf spring, a biasing arm, or a resilient elastomeric member.

In yet another embodiment of the present disclosure, a delivery system of delivering a leadless pacemaker is provided. The delivery system includes a catheter including a distal end, a proximal end opposite the distal end, a lumen extending between the proximal end and the distal end, and a locking hub operably coupled to the proximal end. The locking hub includes an annular member that in turn includes a lumen segment of the lumen.

In one implementation, the locking hub includes one or more buttons and actuating the locking hub includes depressing the one or more buttons. In certain implementations depressing the one or more buttons causes translation of the one or more buttons in a transverse direction relative to a longitudinal axis of the catheter.

In another implementation, the annular member is compressible such that the diameter of the lumen segment varies in response to a compressive force applied to the annular member. In certain implementations the locking hub further includes a movable member adjacent the annular member, the locking hub biased to reduce the diameter of the lumen segment by biasing the movable member in a first direction to compress the annular member. In such implementations, actuating the locking hub may include translating the movable member in a second direction opposite the first direction, thereby reducing compression of the annular member by the movable member. The locking hub may include a biasing element for biasing the movable member in the first direction, the biasing element including one or more of a helical spring, a leaf spring, a biasing arm, or a resilient elastomeric member.

In another embodiment, a delivery system for delivering a leadless pacemaker is provided. The delivery system includes a catheter, which may be a guide catheter. The catheter includes a distal end, a proximal end opposite the distal end, a lumen extending between the distal end and the proximal end, and a locking hub operably coupled to the proximal end. The locking hub includes a lumen segment of the lumen. Self-biasing of the lumen segment places the lumen segment out of alignment with a rest of the lumen. Deflecting the lumen segment against the self-biasing of the lumen segment places the lumen segment in coaxial alignment with the rest of the lumen.

In one implementation, a portion of an inner circumferential surface of the lumen segment is made of a first material, a second portion of the inner circumferential surface of the lumen segment is made of a second material that has a higher coefficient of friction than the first material, and the second material is compressed against an elongated body extending through the lumen when the lumen segment self-biases out of alignment with the rest of the lumen. The first portion may be semi-cylindrical and the second portion may be semi-cylindrical. The elongated body may include a shaft of a deflectable catheter, the shaft including a distal end and proximal end opposite the distal end. The distal end of the shaft is configured to detachably couple to the leadless pacemaker. The shaft is configured to extend through the lumen of the guide catheter.

In one implementation, a portion of an inner circumferential surface of the lumen segment is made of a first material, a second portion of the inner circumferential surface of the lumen segment is made of a second material that is softer than the first material, and the second material is compressed against an elongated body extending through the lumen when the lumen segment self-biases out of alignment with the rest of the lumen. The first portion may be semi-cylindrical and the second portion may be semi-cylindrical. The elongated body may include a shaft of a deflectable catheter, the shaft including a distal end and proximal end opposite the distal end. The distal end of the shaft is configured to detachably couple to the leadless pacemaker. The shaft is configured to extend through the lumen of the guide catheter.

In one implementation, the locking hub further includes a button through which the lumen segment extends, a body supporting the button, and a biasing mechanism acting between the button and the body to self-bias the button such that the lumen segment is out of alignment with the rest of the lumen. The biasing mechanism may include at least one of a helical spring, a leaf spring, a biasing arm extending from the button and acting against the body, a biasing arm extending from the body and acting against the button, or a resilient elastomeric member.

In one implementation, the button and body both include respective stop limit structures that abut when the button is forced against the self-biasing mechanism to the extent that the lumen segment is in coaxial alignment with the rest of the lumen.

In one implementation, a portion of an inner circumferential surface of the lumen segment is made of a first material forming the button. A second portion of the inner circumferential surface of the lumen segment is made of a second material different from the first material and at least one of injected, inserted or molded into a void defined in the first material. The second material is compressed against an elongated body extending through the lumen when the lumen segment self-biases out of alignment with the rest of the lumen.

Also disclosed herein is a delivery system for delivering a leadless pacemaker. In one embodiment, the delivery system includes a catheter. The catheter includes a distal end, a proximal end opposite the distal end, a lumen extending between the distal end and the proximal end, and a locking hub operably coupled to the proximal end, the locking hub including a lumen segment of the lumen. The lumen segment includes a first portion of an inner circumferential surface of the lumen segment made of a first material, and a second portion of an inner circumferential surface of the lumen segment made of a second material different from the first material. The lumen segment is displaceable between a first state and a second state, the first state being where the lumen segment is out of alignment with the rest of the lumen and the second state being where the lumen segment is in coaxial alignment with the rest of the lumen.

In one implementation, the lumen segment is biased in the first state and needs to be forced into the second state. The first material compresses against a tubular body extending through the lumen when in the first state. The first material may be softer than the second material. The first material may have a higher coefficient of friction than the second material.

In another implementation, the locking hub further includes a button through which the lumen segment extends, a body supporting the button, and a biasing mechanism acting between the button and the body to bias the button into the first state. The biasing mechanism may include at least one of a helical spring, a leaf spring, a biasing arm extending from the button and acting against the body, a biasing arm extending from the body and acting against the button, or a resilient elastomeric member. The button and body may both include respective stop limit structures that abut when the button is forced against the biasing mechanism to the extent that the lumen segment is in coaxial alignment with the rest of the lumen.

Depending on the embodiment, the first material may be injected, inserted or molded into a void defined in the second material.

In yet another embodiment of the present disclosure a delivery system for delivering a leadless pacemaker is provided. The delivery system includes a catheter including a distal end, a proximal end opposite the distal end, a lumen extending between the distal end and the proximal end, and a locking hub operably coupled to the proximal end, the locking hub including a lumen segment of the lumen. Self-biasing of the lumen segment reduces a diameter of the lumen segment to a first diameter, the first diameter less than a diameter of a rest of the lumen. Actuating the locking hub increases the diameter of the lumen segment from the first diameter to a second diameter.

In one implementation, the locking hub includes a locking hub body, a compressible seal disposed within the locking hub body and including the lumen segment, the diameter of the lumen segment modifiable by compressing the compressible seal. The locking hub further includes a shuttle movable within the locking hub body. In such implementations, self-biasing of the locking hub includes biasing the shuttle in a first direction to compress the compressible seal, and actuating the locking hub translates the shuttle is in a second direction opposite the first direction, thereby reducing compression of the compressible seal. The locking hub may further include one or more buttons, the locking hub being actuatable to translate the shuttle by depressing the one or more buttons. In such implementations, depressing the one or more buttons may translate the one or more buttons transversely toward a longitudinal axis of the catheter.

Each of the one or more buttons may include one or more wedged protrusions and the shuttle may further include angled indentations shaped to receive each of the one or more wedged protrusions when the one or more buttons are depressed. Receipt of the wedged protrusions by the angled indentations in such implementations results in translation of the shuttle in the second direction.

The locking hub may further include a biasing element configured to bias the shuttle in the first direction. The biasing element may include, without limitation, at least one of a helical spring, a leaf spring, a biasing arm, a biasing arm, or a resilient elastomeric member.

In certain implementations, the compressible seal includes a proximal cylindrical section and a distal tapered section. In such implementations the locking hub body may include a proximal cylindrical inner surface and a distal tapered inner surface such that, when the compressible seal is disposed within the locking hub body, the proximal cylindrical section of the compressible seal is within the proximal cylindrical inner surface and the distal tapered section of the seal is adjacent the distal tapered inner surface. When the shuttle is biased against the compressible seal in such implementations, the distal tapered section of the compressible seal may abuts the distal tapered inner surface of the hub body, thereby reducing the diameter of the lumen segment.

The shuttle may include a plurality of ribs disposed within respective channels of the locking hub body.

In certain implementations, the locking hub may include a cap coupled to a proximal end of the locking hub. Such coupling may be achieved by one or more of ultrasonic welding, an adhesive, a snap fit, and a pinned coupling.

In another embodiment of the present disclosure, a delivery system for a leadless pacemaker is provided. The delivery system includes a catheter including a distal end, a proximal end opposite the distal end, a lumen extending between the distal end and the proximal end, and a locking hub operably coupled to the proximal end, the locking hub comprising a seal element including a lumen segment of the lumen. Self-biasing of the locking hub compresses the seal element, thereby reducing a diameter of the lumen segment. Actuation of the locking hub reduces the compression of the seal element.

In one implementation, the locking hub includes a movable shuttle and the self-biasing of the locking hub biases the shuttle in a first direction to compress the seal element, the first direction being along a longitudinal axis of the catheter.

In such an implementation, actuation of the locking hub translates the shuttle in a second direction opposite the first direction. The locking hub may further include a biasing element configured to bias the shuttle in the first direction, the biasing element including at least one of a helical spring, a leaf spring, a biasing arm, a biasing arm, or a resilient elastomeric member.

In another implementation, actuation of the locking hub comprises depressing one or more buttons of the locking hub such that the one or more buttons translate transversely and inward relative to the longitudinal axis of the catheter.

In yet another implementation, the locking hub includes a locking hub body having a tapered inner surface and the seal includes a corresponding tapered outer surface. In such implementations, the self-biasing may apply a longitudinal force to the seal element such that an interface between the tapered inner surface of the locking hub body and the tapered outer surface of the seal element causes transverse compression of the seal element toward a longitudinal axis of the catheter.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 1A-1B are, respectively, side and end views of an example leadless cardiac pacemaker.

FIGS. 4A-4G are side views of a delivery system attached to a pacemaker.

FIGS. 5A-5D are various views of a catheter handle and tether key.

DETAILED DESCRIPTION

Figure 1C:
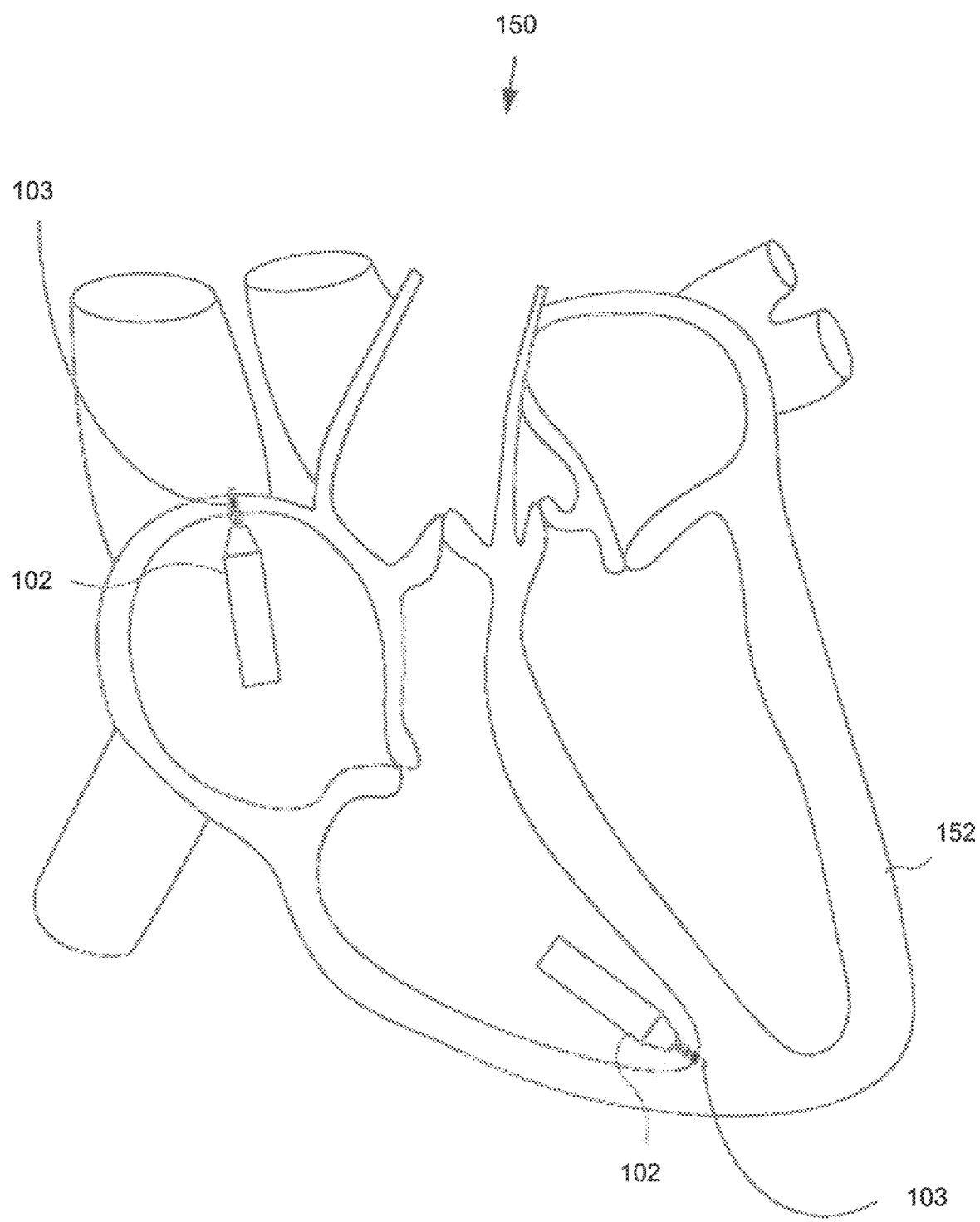
FIG. 1C is a diagrammatic medial-lateral cross section of a patient heart illustrating example implantation of leadless pacemakers in the patient heart.

The present disclosure is directed to a delivery system and associated methodology for delivering a leadless pacemaker to an implantation site in a patient. The delivery system includes a locking hub of a guide catheter that allows for coarse and fine adjustment of positioning of the guide catheter relative to a deflectable catheter extending through the guide catheter, the leadless pacemaker being supported off of the distal end of the deflectable catheter.

As discussed in detail below, in one embodiment, the locking hub includes a compression button with a lumen section extending along its length that is slightly larger in diameter than the diameter of the shaft of the deflectable catheter that extends through the guide catheter and its locking hub. Half of the inner circumferential surface of the lumen section is a hard, low friction material, and the other half of the inner circumferential surface of the lumen section is a soft, high friction material. Unless acted upon by the user, the compression button self-biases such that the lumen section is out of alignment with the rest of the lumen of the guide catheter, thereby causing the soft, high friction material to compress against the shaft of the deflectable catheter and locking the shaft relative to the locking hub. When the user depresses the compression button, the lumen section is caused to align with the rest of the lumen of the guide catheter in a coaxial arrangement, thereby making it possible for the shaft of the deflectable catheter to readily displace through the locking hub and the rest of the guide catheter.

In another embodiment, the locking hub includes a compressible seal with a lumen section extending along its length. When the seal is compressed, the diameter of the lumen segment is reduced such that compressible seal engages an outer surface of a shaft or similar elongate body of the catheter extending through the lumen. The seal is biased into compression by a shuttle acted upon by a biasing element, such as a helical spring. When a user depresses compression buttons of the locking hub, the shuttle is translated away from the seal, thereby allowing the seal to decompress. Such decompression causes the diameter of the lumen segment to expand, reducing the engagement between the seal and the elongate body and allowing movement of the elongate body relative to the locking hub.

Before beginning a detailed discussion of the locking hub and associated method, a general overview of an example leadless pacemaker and catheter-based delivery system is provided as follows.

a. Overview of Leadless Pacemaker and a Catheter-Based Delivery System

FIGS. 1A-1B illustrate an example leadless cardiac pacemaker 102. The leadless pacemaker 102 can communicate by conducted communication, representing a substantial departure from conventional pacing systems. The leadless pacemaker can perform cardiac pacing that has many of the advantages of conventional cardiac pacemakers while extending performance, functionality, and operating characteristics with one or more of several improvements.

In some embodiments of a cardiac pacing system, cardiac pacing is provided without a pulse generator located in the pectoral region or abdomen, without an electrode-lead separate from the pulse generator, without a communication coil or antenna, and without an additional requirement of battery power for transmitted communication.

FIG. 1C illustrates an embodiment of a cardiac pacing system 150 configured to attain these characteristics. The cardiac pacing system 150 includes one or more leadless cardiac pacemakers 102. Each leadless pacemaker is substantially enclosed in a hermetic housing 151 suitable for placement on or attachment to the inside or outside of a cardiac chamber, such as the right atrium and/or right ventricle of the patient heart 152, as can be understood from FIG. 1B. Attachment of a leadless pacemaker to the cardiac tissue can be accomplished via a helical anchor 103 on an anchor mount 155 extending from a distal end of the leadless pacemaker.

As can be understood from FIGS. 1A-1B, the leadless pacemaker 102 can have two or more electrodes 154, 156 located within, on, or near the housing 151, for delivering pacing pulses to muscle of the cardiac chamber and optionally for sensing electrical activity from the muscle, and for bidirectional communication with at least one other device within or outside the body. The housing can contain a primary battery to provide power for pacing, sensing, and communication, for example bidirectional communication. The housing 151 can optionally contain circuits for sensing cardiac activity from the electrodes 154, 156. The housing contains circuits for receiving information from at least one other device via the electrodes and contains circuits for generating pacing pulses for delivery via the electrodes. The housing can optionally contain circuits for transmitting information to at least one other device via the electrodes and can optionally contain circuits for monitoring device health. The housing contains circuits for controlling these operations in a predetermined manner.

In some embodiments, a cardiac pacemaker can be adapted for delivery and implantation into tissue in the human body. In a particular embodiment, a leadless cardiac pacemaker can be adapted for implantation adjacent to heart tissue on the inside or outside wall of a cardiac chamber, using two or more electrodes located on or within the housing of the pacemaker, for pacing the cardiac chamber upon receiving a triggering signal from at least one other device within the body.

Leadless pacemakers or other leadless biostimulators are typically fixed to an intracardial implant site by an actively engaging mechanism or primary fixation mechanism such as a screw or helical member 103 that screws into the myocardium. Examples of such leadless biostimulators are described in the following publications, the disclosures of which are incorporated by reference: (1) U.S. Pat. No. 8,457,742, issued on Jun. 4, 2013, entitled "Leadless Cardiac Pacemaker System For Usage In Combination With An Implantable Cardioverter-Defibrillator"; (2) U.S. Pat. No. 9,358,400 issued on Jul. 7, 2016, entitled "Leadless Cardiac Pacemaker"; (3) U.S. Pat. No. 9,216,298, issued on Dec. 22, 2015, entitled "Leadless Cardiac Pacemaker System with Conductive Communication"; (4) U.S. Pat. No. 8,352,025 issued on Jan. 8, 2013, entitled "Leadless Cardiac Pacemaker Triggered by Conductive Communication"; (5) U.S. Pat. No. 7,937,148 issued on May 3, 2011, entitled "Rate Responsive Leadless Cardiac Pacemaker"; (6) U.S. Pat. No. 7,945,333 Issued on May 17, 2011, entitled "Programmer for Biostimulator System"; (7) U.S. Pat. No. 8,010,209, issued on Aug. 30, 2011, entitled "Delivery System for Implantable Biostimulator"; and (8) International Application No. PCT/US2006/040564, filed on Oct. 13, 2006, entitled "Leadless Cardiac Pacemaker and System" and published as WO07047681A2 on Apr. 26, 2007.

In addition to the primary fixation mechanism, such as a helix, some leadless biostimulators may further include a secondary fixation mechanism to provide another feature for keeping the leadless biostimulator in place within the body. Secondary fixation mechanisms can be either active (e.g., the secondary fixation mechanism can actively engage tissue, either within or outside the heart), or can be passive (e.g., the secondary fixation mechanism is not attached to tissue but rather prevents the leadless biostimulator from moving around in the body in the case of accidental detachment). Further details on secondary fixation mechanisms can be found in U.S. Pat. No. 8,527,068, issued on Sep. 3, 2013.

Leadless pacemakers or other leadless biostimulators can be delivered to and retrieved from a patient using any of the delivery systems described herein. In some embodiments, a leadless pacemaker is attached or connected to a delivery system and advanced intravenously into the heart. The delivery system can include features to engage the leadless pacemaker to allow fixation of the leadless pacemaker to tissue. For example, in embodiments where the leadless pacemaker includes an active engaging mechanism, such as a screw or helical member, the delivery system can include a docking cap or key configured to engage the leadless pacemaker and apply torque to screw the active engaging mechanism into the tissue. In other embodiments, the delivery system includes clips designed to match the shape of a feature on the leadless pacemaker and apply torque to screw the active engaging mechanism into the tissue.

Figure 1D:
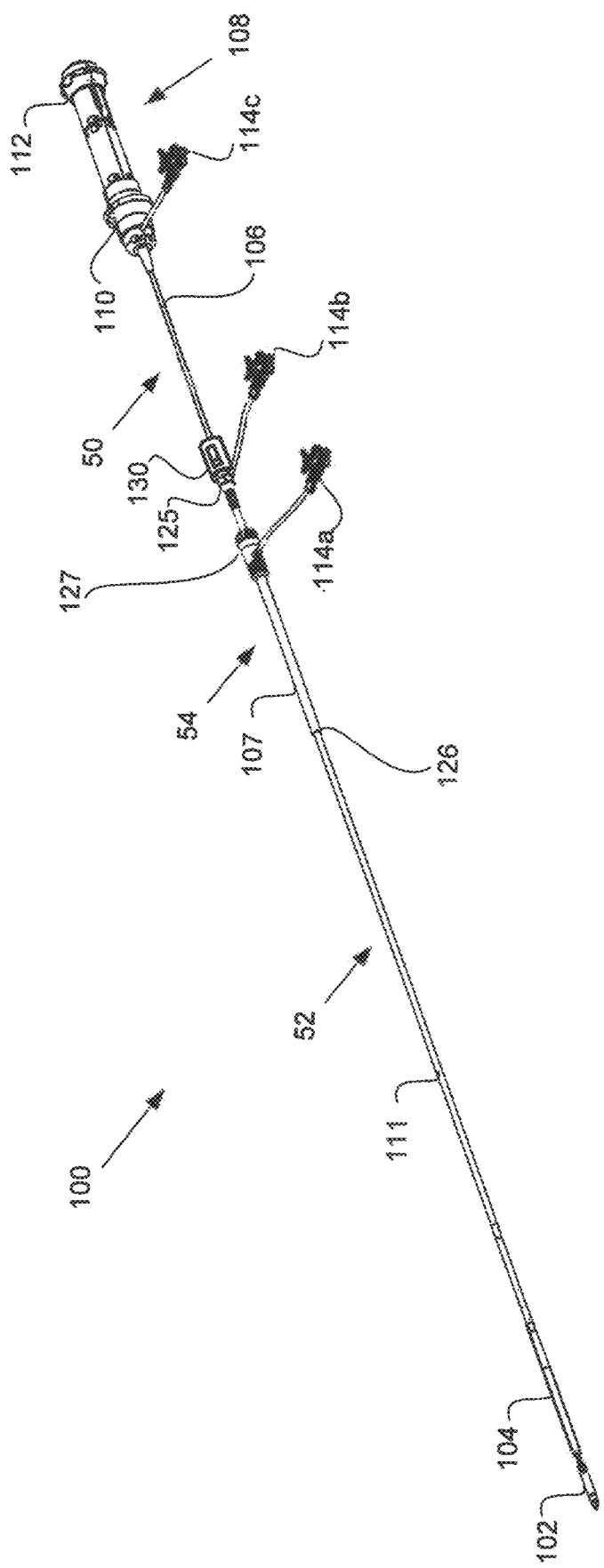
FIG. 1D is one embodiment of a delivery system for delivering a leadless pacemaker.

FIG. 1D illustrates a pacemaker delivery system 100 configured for delivery of a leadless pacemaker 102 into a patient. The delivery system 100 can include a deflectable catheter 50, a guide catheter 52, and an introducer sheath 54. As can be understood from FIG. 1D, the deflectable catheter 50 extends through the guide catheter 52 and includes a distal end and a proximal end. The distal end of the deflectable catheter is selectively connectable to the proximal end of the leadless pacemaker 102 and the proximal end of the deflectable catheter includes a handle 108 by which the user may cause the deflectable catheter shaft 106 to distally-proximally displace within the length of the guide catheter and, further, by which the user may actuate the distal end of the deflectable catheter to selectively connect and disconnect from a proximal end of the leadless pacemaker. The deflectable catheter 50 extends from both the distal and proximal ends of the guide catheter 52.

Figure 1E:
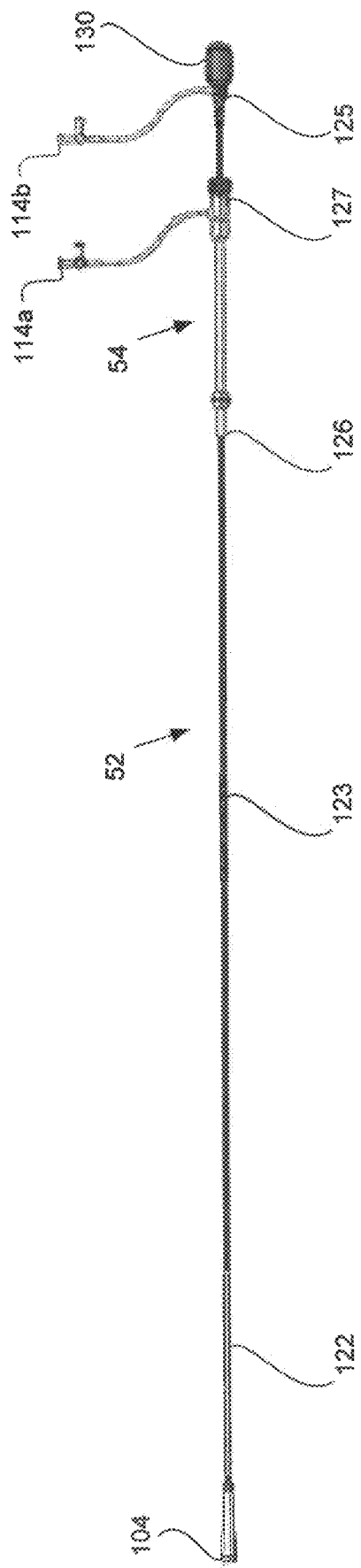
FIG. 1E illustrates only the guide catheter and introducer sheath of the pacemaker delivery system of FIG. 1D.

FIG. 1E illustrates only the guide catheter 52 and introducer sheath 54 of the pacemaker delivery system 100 of FIG. 1D. As can be understood from FIGS. 1D and 1E, the guide catheter 52 extends through the introducer sheath 51 and includes a distal end and a proximal end. The distal end of the guide catheter 52 includes a protective pacemaker sheath 104 discussed in greater detail below. The proximal end of the guide catheter includes a flush port 114b extending from a proximal hub 125 and a locking hub 130 proximally extending from the proximal hub 125. While the locking hub 130 is shown as located adjacent the proximal hub 125, in other embodiments the locking hub 130 may be located at other locations on the guide catheter. The locking hub 130 is discussed in detail below.

As shown in FIGS. 1D and 1E, the guide catheter 52 extends from both the distal and proximal ends of the introducer sheath 54. As shown in FIG. 1E, the shaft 111 of the guide catheter 52 includes a distal soft durometer section 122 and a proximal high durometer section 123 that is longer than the distal soft durometer section.

As depicted in FIGS. 1D and 1E, introducer sheath 54 includes a distal end 126 and a proximal end. The proximal end of the introducer includes a flush port 114a and a hub 127.

As can be understood from FIGS. 1D and 1E and for purposes of discussion, the pacemaker delivery system 100 may be considered to include the various components of the deflectable catheter 50, the guide catheter 52 and the introducer 54. For example, the pacemaker delivery system 100 may be considered to include the pacemaker sheath 104, guide catheter shaft 111, pacemaker introducer sheath 107, handle 108, deflection knob 110, tether shuttle 112, and flush ports 114a, 114b, and 114c The deflection knob 110 can be used to steer and guide the catheter during implantation and/or removal of the pacemaker. The flush ports 114a, 114b, and 114c can be used to flush saline or other fluids through the catheter. Sheath 107 can be advanced distally over catheter shaft 111 to provide additional steering and support for the delivery catheter during implantation and to surround the pacemaker as it is introduced through a trocar or introducer into the patient.

Figure 2A:
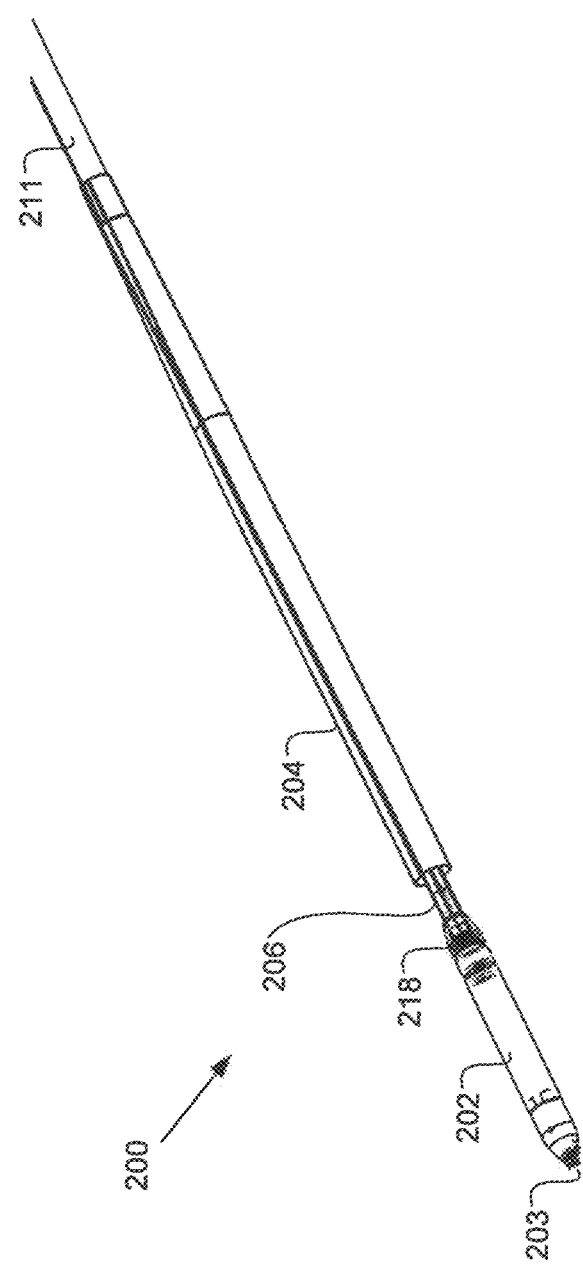
FIGS. 2A-2B are close-up views of a distal portion of the delivery system.
Figure 2B:
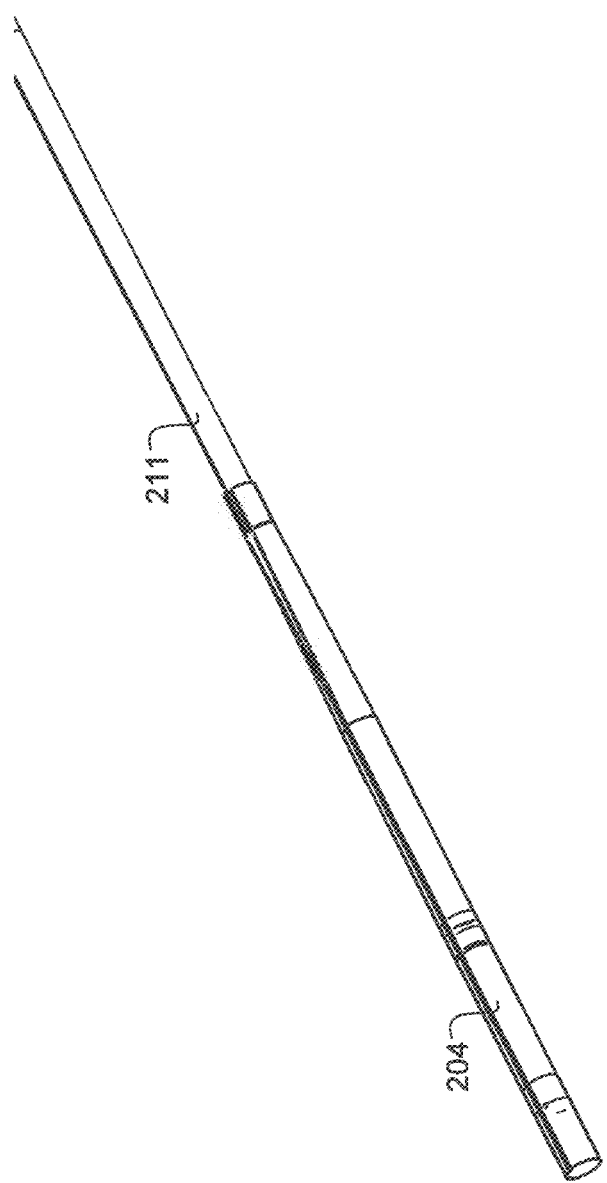

FIG. 2A is a close-up view of a distal portion of delivery system 200 and pacemaker 202. The pacemaker of FIG. 2A can include a helix 203 for attachment of the pacemaker to tissue. In FIG. 2A, the pacemaker is attached to docking cap 218 of catheter shaft 206. Pacemaker sheath 204 is shown pulled back proximally along catheter shaft 206 and guide catheter shaft 211 to expose the pacemaker 202 and helix 203. In FIG. 2B, pacemaker sheath 204 is extended distally along guide catheter shaft 211 to cover the catheter shaft 206, pacemaker 202, and helix to protect the tissue from the sharp edges of the helix during implantation. When the pacemaker sheath is pulled back proximally, as shown in FIG. 2A, the pacemaker 202 is in an exposed, delivery configuration. When the pacemaker sheath is advanced distally to protect the pacemaker and helix, as shown in FIG. 2B, the pacemaker 202 is in a protected, advancement configuration.

Figure 3A:
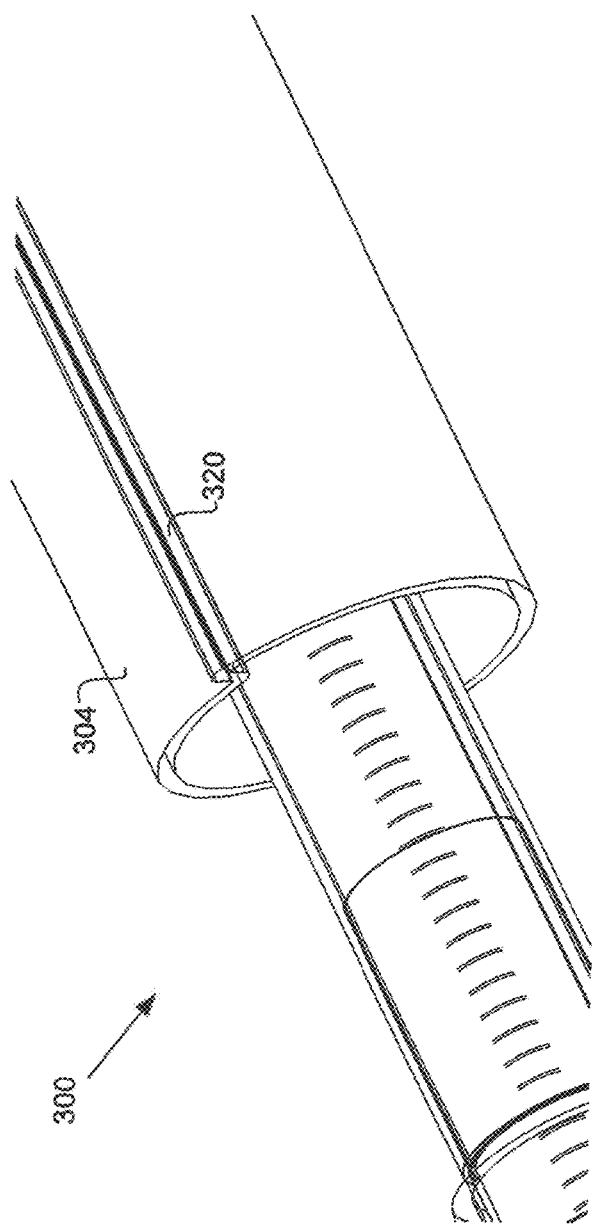
FIGS. 3A-3B are schematic side and cross-sectional views of a pacemaker sheath.
Figure 3B:
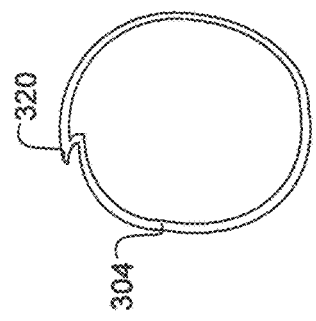

FIGS. 3A-3B are close-up and cross sectional views of pacemaker sheath 304 of delivery system 300. As shown, pacemaker sheath 304 can include crease or fold 320 along the length of the sheath. During initial insertion of the delivery system into a patient, a physician can gain access to the patient's venous system with an introducer sheath using the Seldinger technique (not shown). The delivery system, including the leadless pacemaker and catheter shaft, can then be advanced through the introducer sheath into the patient's venous system to facilitate delivery of the pacemaker into the heart. Reducing the diameter of the pacemaker, the delivery system, and thus the introducer sheath, provides for easier and less intrusive access to a patient's venous system.

By designing pacemaker sheath 304 with a fold 320 that runs longitudinally along the sheath, the cross sectional diameter of the pacemaker sheath can be reduced by folding the sheath over itself. Thus, during initial implantation of the pacemaker through a introducer sheath into the patient, the pacemaker sheath can be positioned just proximally to the pacemaker, and folded along fold 320 so as to have a cross sectional diameter close to or equal to the same diameter as the pacemaker. This allows a smaller diameter introducer sheath to be used than would normally be necessary, since those delivery systems must incorporate a larger introducer sheath to allow passage of a full sized pacemaker sheath. After the delivery system is inserted through the introducer sheath into the patient, the sheath can be advanced distally over the leadless pacemaker. Advancing the pacemaker sheath distally causes fold 320 to unfold, thereby increasing the diameter of the pacemaker sheath so that it can slide over and cover the pacemaker and fixation helix. FIG. 3B is a cross sectional view of the pacemaker helix 304 and fold 320, giving another view on how the cross sectional diameter of the pacemaker sheath can increase and decrease.

FIG. 4A illustrates delivery system 400, including pacemaker 402 comprising helix 403 and attachment feature 424, and the delivery catheter comprising pacemaker sheath 404, catheter shaft 406, docking cap 418, and tethers 422a and 422b. The tethers can comprise wires, shafts, tubes, cords, ropes, strings, or other similar structures that can extend throughout the catheter shaft. In some embodiments, the tethers comprise a shape memory material, such as nitinol. In other embodiments, the tethers comprise stainless steel wires or braids. In FIG. 4A, the pacemaker 402 is not attached to docking cap 418 of the delivery catheter. The process of connecting the pacemaker to the delivery catheter will now be described.

Figure 4B:
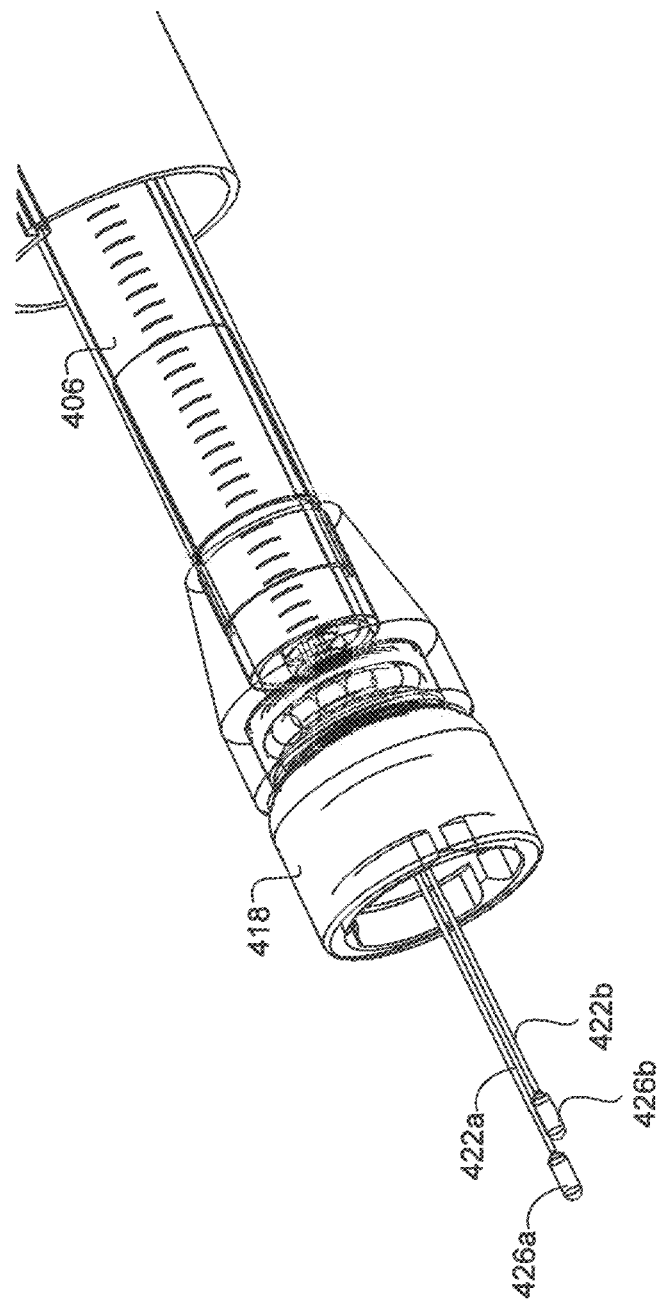

Referring to FIG. 4B, tethers 422a and 422b can include distal features 426a and 426b. The distal features can be, for example, features on the tethers that protrude radially from the tether, such as bumps, spheres, cylinders, rectangles, or other similar shapes extending outwards from the tethers. In some embodiments, the distal features can be expandable, such as balloons or expandable mechanical structures. Generally, the distal features have a cross sectional diameter larger than the cross sectional diameter of the tethers. As shown, in one embodiment, distal feature 422a can be advanced further from the catheter than distal feature 422b, so that when the tethers are pushed together, distal feature 422b rests against tether 422a. This causes the combined cross sectional diameter of both distal features and tethers to be less than if the distal features were lined up side by side. By way of comparison, in FIG. 4C the distal features 426a and 426b are lined up side by side and therefore have a greater combined cross sectional diameter when pressed together than is shown in FIG. 4B.

Figure 4C:
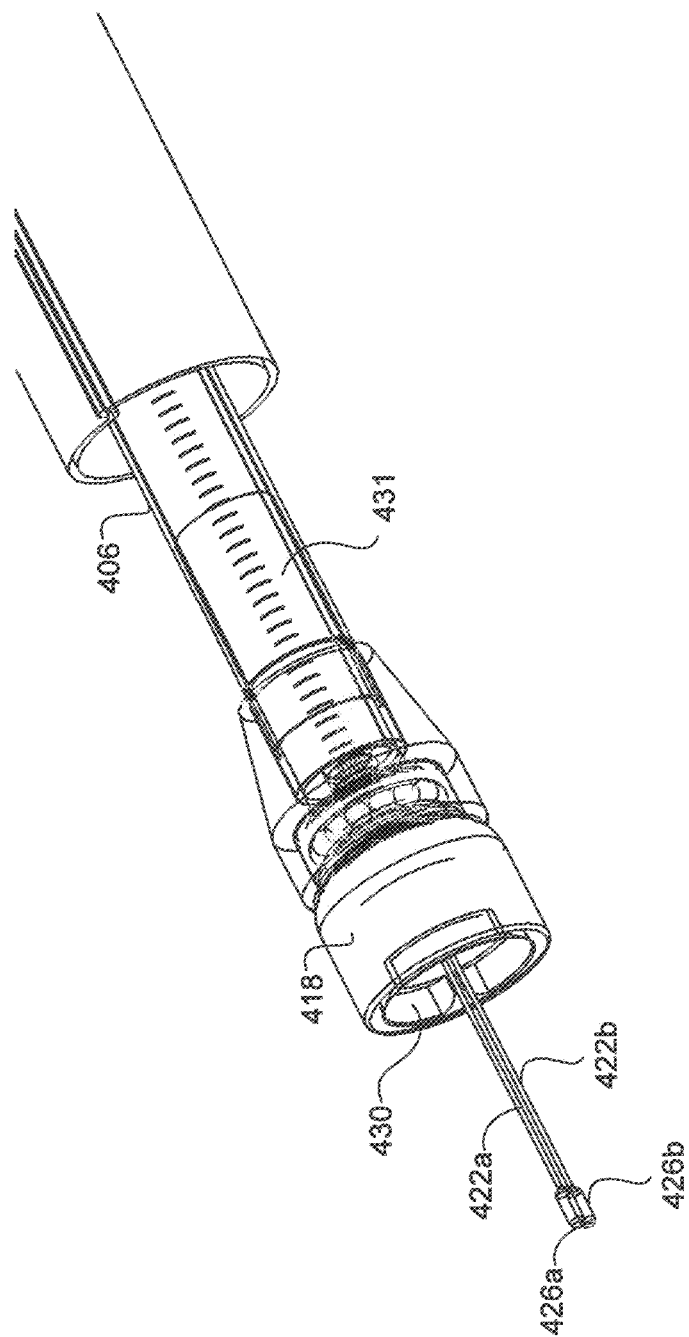
Figure 4D:
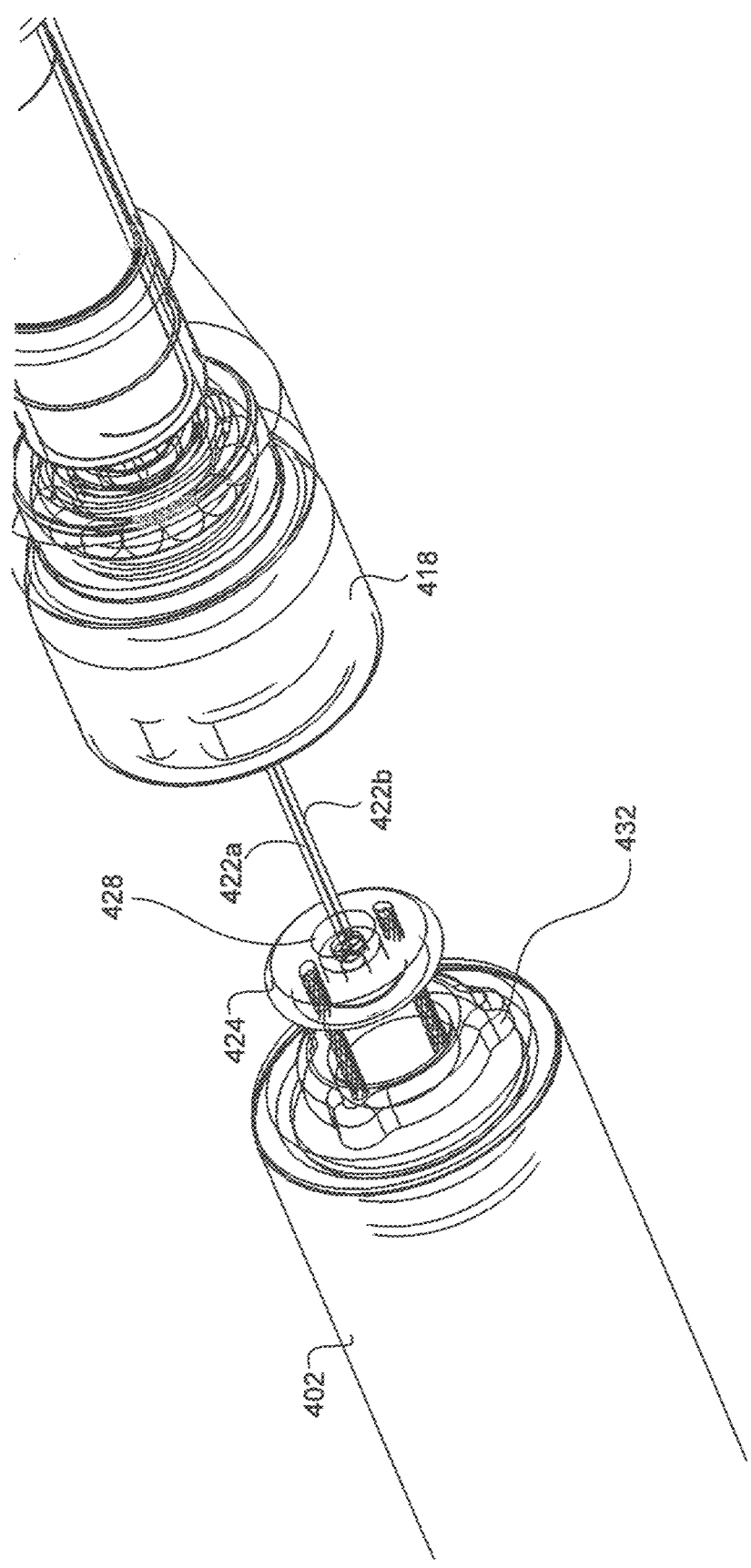
Figure 4E:
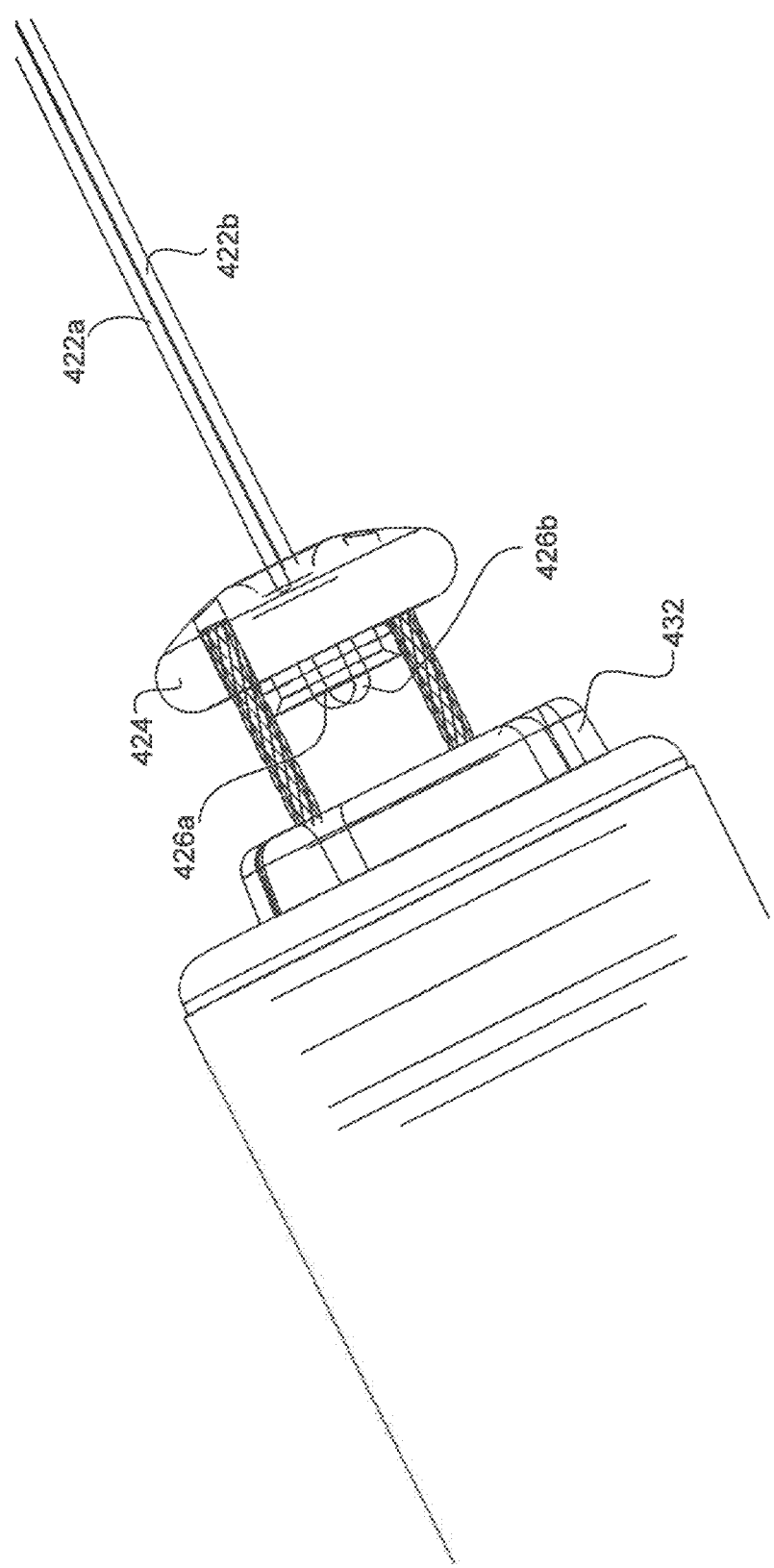
Figure 4F:
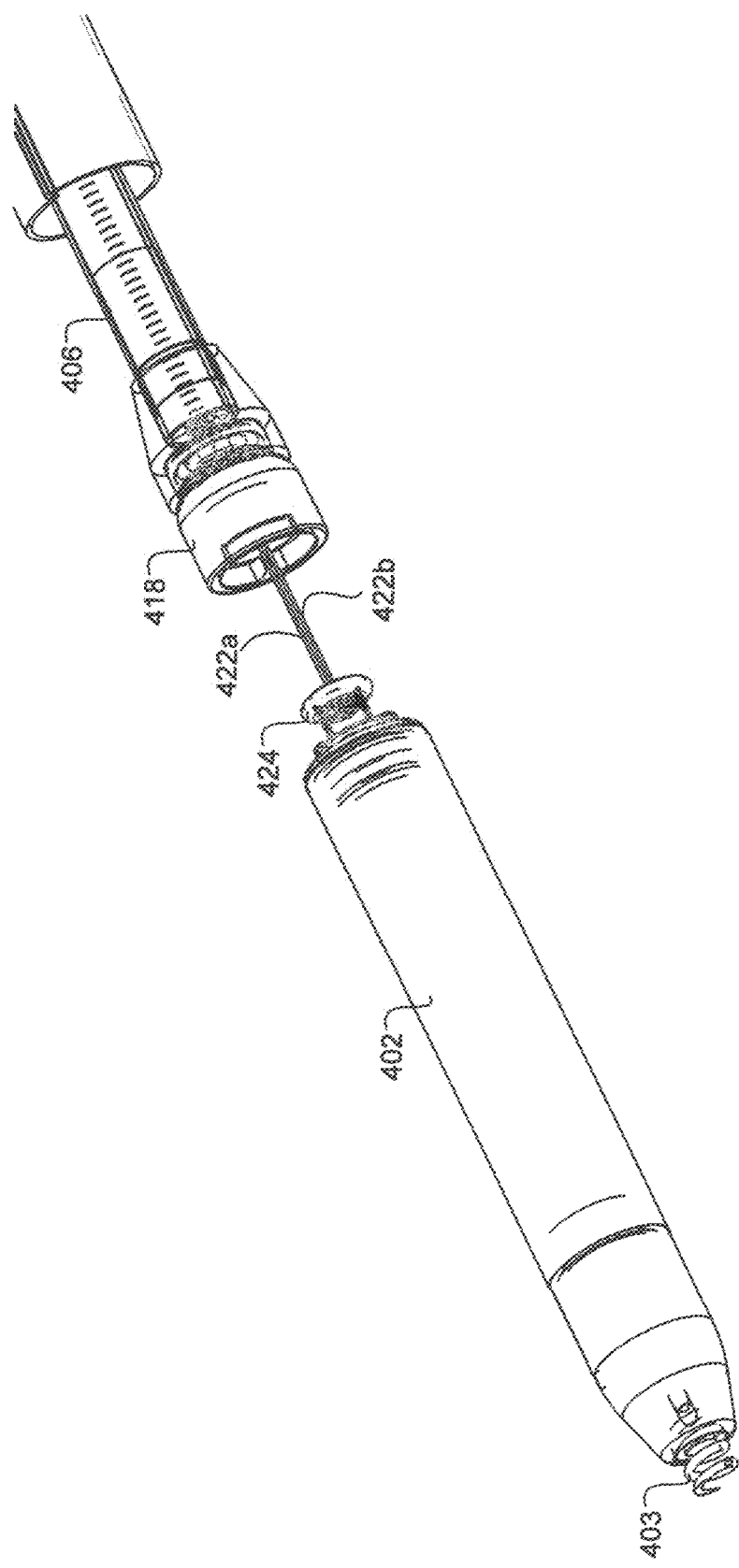

The length of tethers 422a and 422b, and thus the position of distal features 426a and 426b, can be adjusted so that distal features 426a and 426b are not aligned in a side by side configuration (e.g., the un-aligned configuration shown in FIGS. 4A-4B). When the tethers and distal features are in this un-aligned configuration, the cross sectional diameter of the distal features is reduced since the distal features are not positioned side by side. The tether distal features 426a and 426b can then be advanced in this un-aligned configuration through hole 428 of attachment feature 424, as shown in FIGS. 4D-4F. In this embodiment, the diameter of hole 428 should be sufficiently large enough to allow the distal features 426a and 426b of tethers 422a and 422b to pass when in the un-aligned configuration. Upon passing the distal features through the hole 428, the length of the tethers can then be adjusted to align the distal features in the side by side configuration (e.g., as shown in FIGS. 4C and 4E). When the distal features are positioned side by side, the combined cross sectional diameter of the distal features becomes larger than the diameter of hole 428, which essentially locks the tethers and distal features in the attachment feature 424 be preventing the distal features from being able to pass proximally through the hole 428.

Figure 4G:
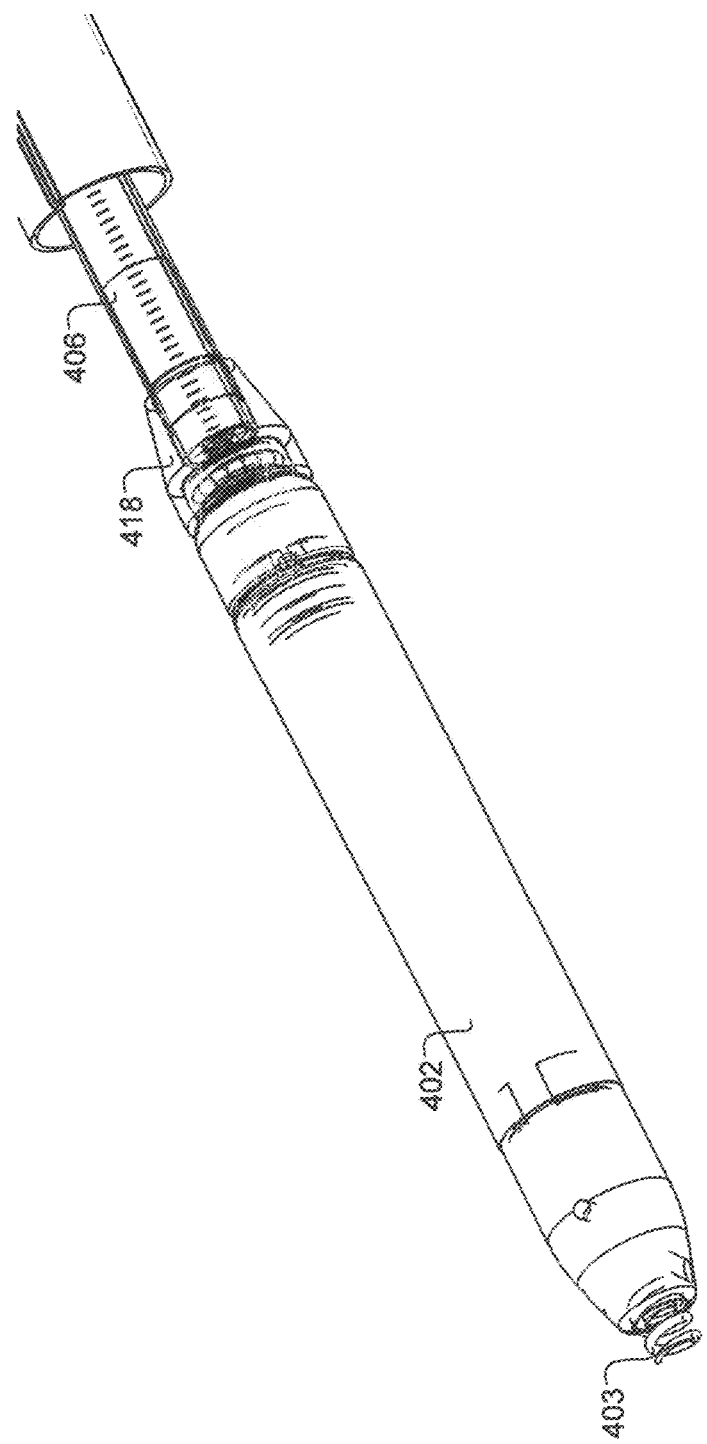

Still referring to FIGS. 4C and 4D, the docking cap 418 of the delivery catheter can include a torque slot 430 (shown in FIG. 4C) sized and configured to mate with a torque key 432 (shown in FIG. 4D) disposed on a proximal end of the pacemaker. The torque slot 430 can be coupled to a torque shaft 431, which runs the length of the delivery catheter extending into the handle (not shown). In FIGS. 4C and 4D, torque key 430 is shown as a "male" key and torque slot 430 is shown as a "female" key, but it should be understood that in other embodiments, the "male" key can be located on the attachment feature 418, and the "female" key can be disposed on the pacemaker. It should also be appreciated that key 432 and slot 430 can comprise any number of shapes, including, without limitation, square, rectangle, triangle, pentagon, hexagon, cross, or "X", so long as key 432 fits within and can apply rotational torque to slot 430. Once the tethers are locked within the attachment feature, the tethers can be pulled proximally to pull attachment feature 424 and the pacemaker towards the catheter and to attach the pacemaker to the delivery catheter, thereby engaging torque slot 430 with torque key 432 (as shown in FIG. 4G).

Figure 5A:
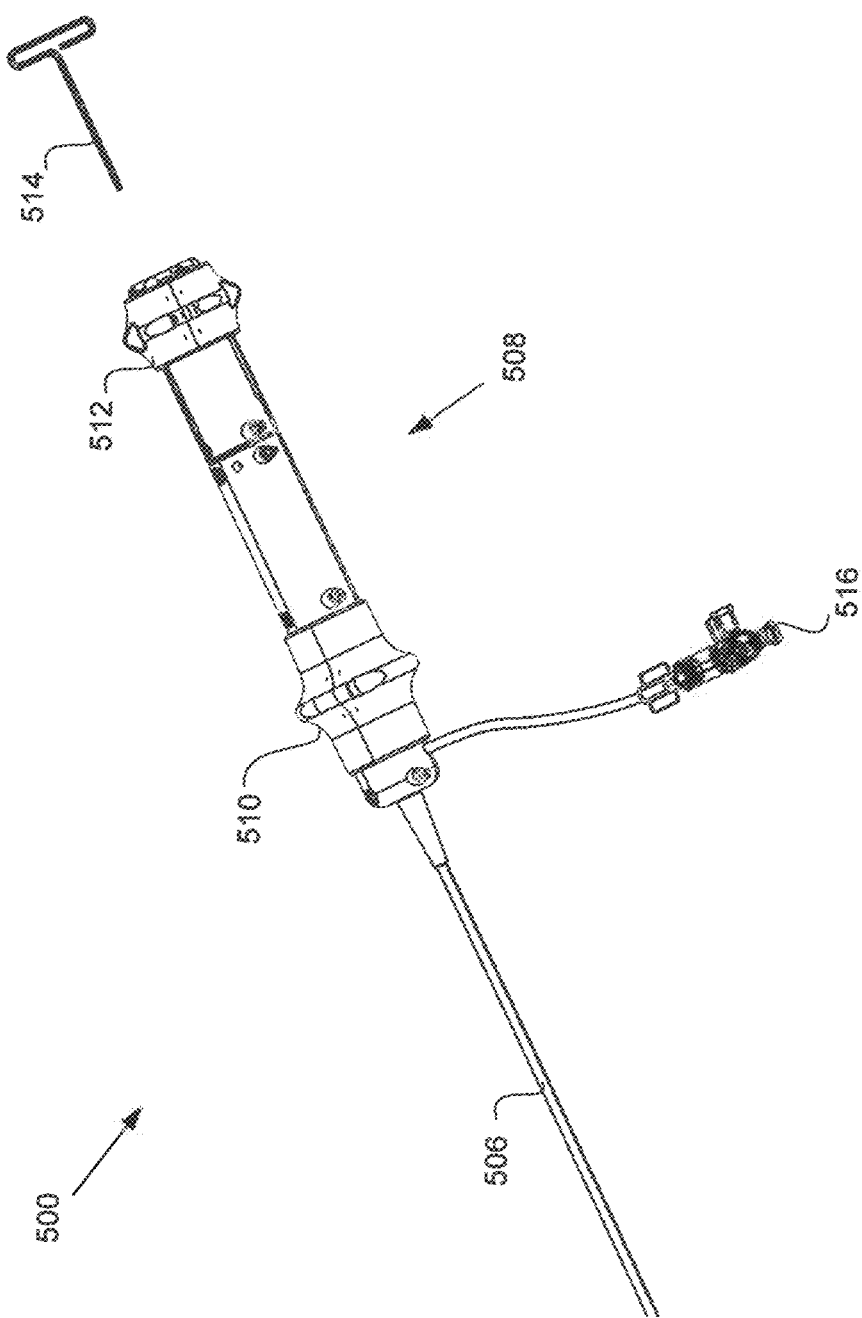
Figure 5B:
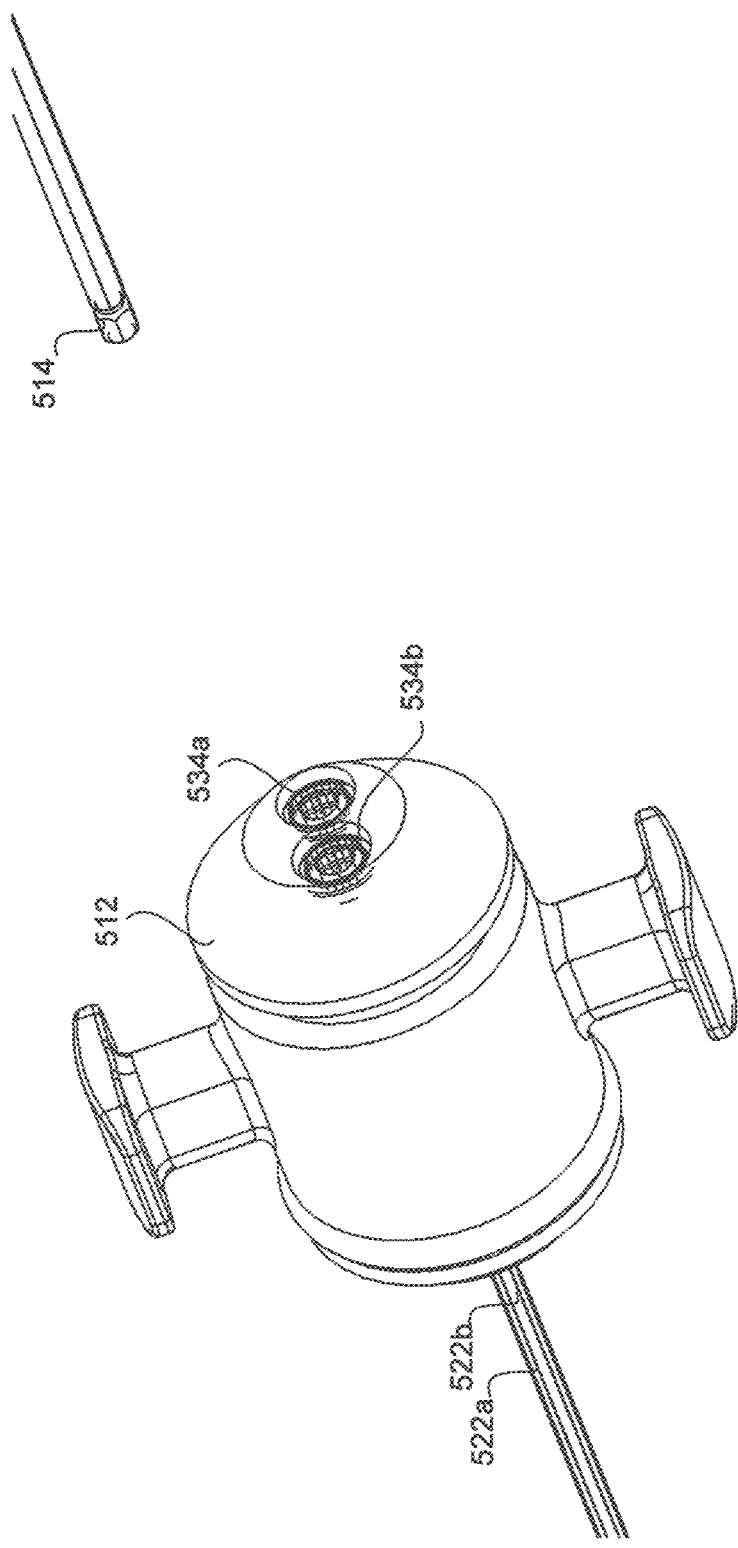

FIGS. 5A-5D are close-up views of handle 508 of delivery system 500. In FIG. 5A, handle 508 includes deflection knob 510, tether knob 512, tether adjustment feature 514, and flush ports 516. As described above, deflection knob 510 provides for steering and guidance of the catheter during implantation and/or removal of the pacemaker. The flush ports 516 can be used to flush saline or other fluids through the catheter. Referring now to FIGS. 5B and 5C, tether adjustment feature 514 can be configured to adjust then length of tethers 522a and 522b that extends distally outwards from the delivery catheter, causing the distal features (not shown) to be in either a side by side "locked" configuration or an un-aligned "unlocked" configuration.

Figure 5D:
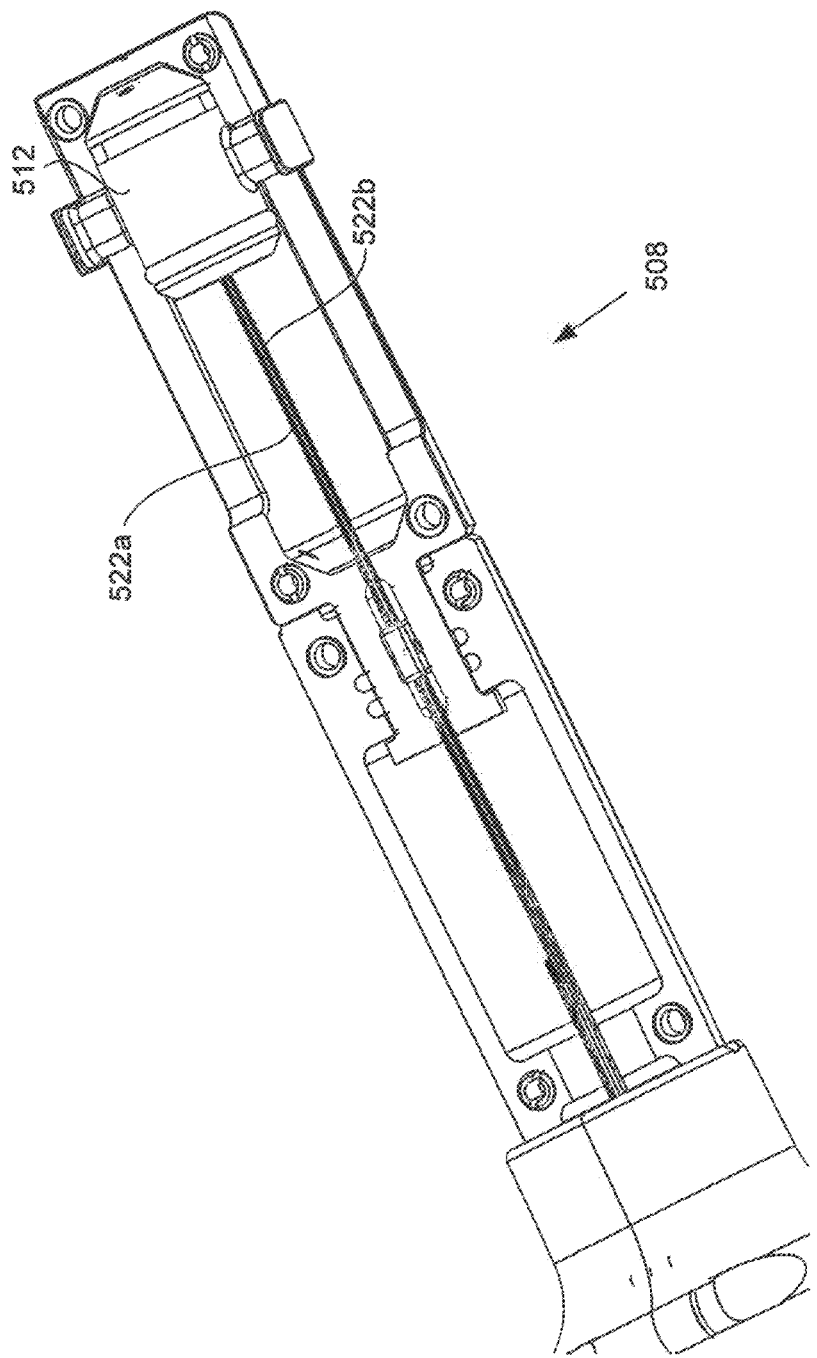

The tether adjustment feature can comprise an Allen wrench or any other suitable key, and can be configured to mate with and engage proximal keys 534a and 534b of tethers 522a and 522b, respectively, which are disposed within shuttle 512. In another embodiment, the tether adjustment feature can comprise knobs or dials on the handle itself, and a user can simply turn the knobs or dials to adjust the length of the tethers. The shuttle can be inserted into handle 508, as shown in FIG. 5D. The proximal keys 534a and 534b of tethers 522a and 522b are shown without shuttle 536 in FIG. 5C for ease of illustration. Rotation of tether adjustment feature 514 causes proximal keys 534a and/or 534b to move distally or proximally within shuttle 512, which therefore changes the length of tethers 522a and/or 522b extending distally from the delivery catheter. Thus, the tether key can be used to either align the distal features of the tethers in a side by side (e.g., locked) configuration, or alternatively, to place the distal features of the tethers in an un-aligned (e.g., unlocked configuration), permitting docking and locking of the pacemaker to the delivery catheter.

Referring back to FIGS. 4D-4G and 5A, it can now be understood how the pacemakers described herein can be delivered and attached to tissue, and then released from the delivery system. In FIGS. 4D-4F, tethers 422a and 422b can be inserted in an "unlocked" or un-aligned configuration into hole 428 of attachment feature 424. The distal features of the tethers can then be aligned so as to lock the distal features in the attachment feature. Referring to FIG. 5A, tether shuttle 512 can then be pulled proximally to cause the tethers to move proximally, thereby docking the pacemaker against the delivery catheter (as shown in FIG. 4G). When the pacemaker is docked against the delivery catheter, torque key 432 of the pacemaker (shown in FIG. 4D) fits within and is mated to torque slot 420 of the delivery catheter (shown in FIG. 4C).

Referring to FIG. 5A, tether shuttle 512 of handle 508 can then be rotated, which rotates torque shaft 431 (shown in FIG. 4C) within the delivery catheter and applies torque to torque slot 430, and thus to torque key 432 on the pacemaker. By rotating the shuttle, and thus the torque shaft, the delivery catheter applies torque to the pacemaker to screw the fixation helix of the pacemaker into tissue. Once the fixation helix is fully inserted into tissue, the tethers can be placed into an un-aligned or "unlocked" configuration with tether adjustment feature 514, allowing the tethers and distal features to be removed from the attachment feature of the pacemaker. Once the delivery catheter is disengaged from the pacemaker, the catheter can be removed from the patient, leaving the pacemaker in place at the target tissue.

Figure 6A:
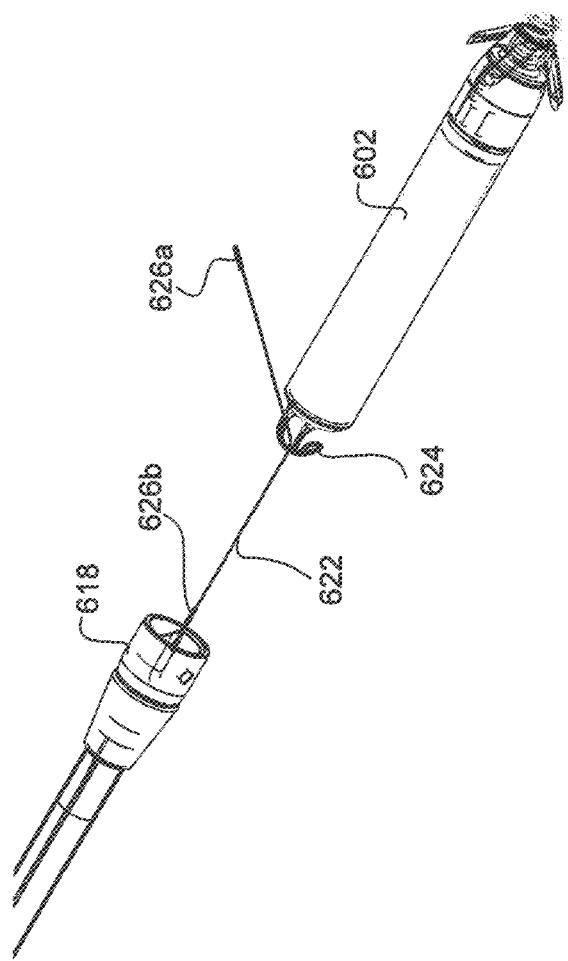
FIGS. 6A-6B are an alternate embodiment of a delivery system having a single tether.
Figure 6B:
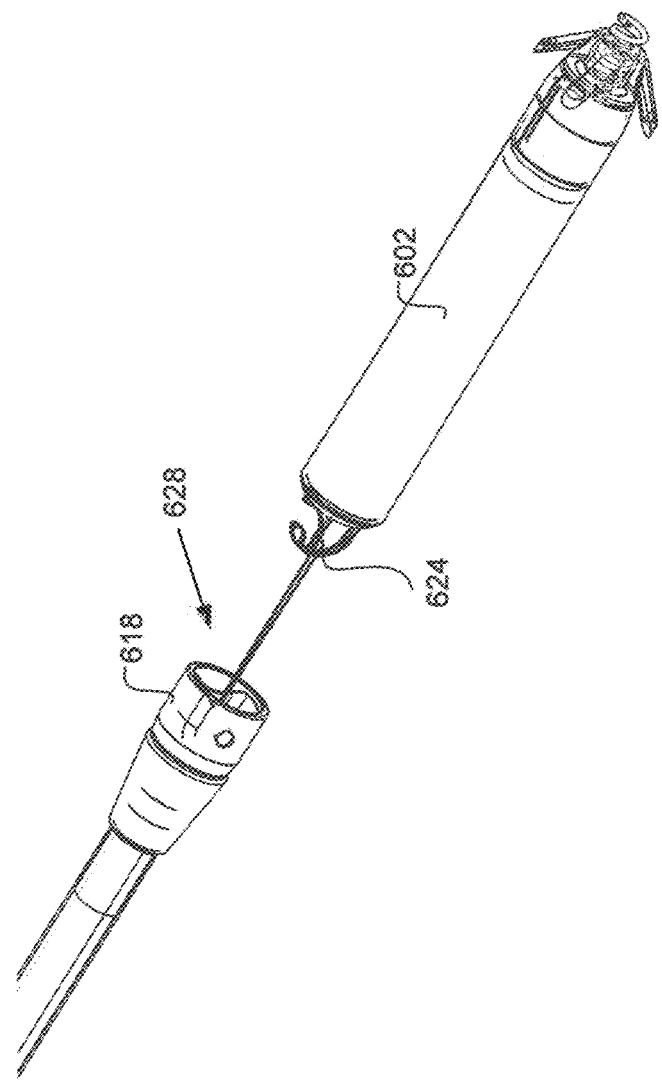

FIGS. 6A and 6B illustrate an alternate embodiment for attaching a delivery catheter to a pacemaker. The embodiment shown in FIGS. 6A and 6B employs a similar concept to that described above. However, instead of using two tethers, as described above, the embodiment of FIGS. 6A and 6B utilizes a single tether 622, having both a distal feature 626a and a proximal feature 626b. In the embodiment of FIGS. 6A and 6B, the tether 622 can comprise a shape memory alloy, such as nitinol, and can include a pre-bent or pre-biased shape. This pre-biased shape can allow the distal feature 626a of the tether to naturally bias outwards, as shown in FIG. 6A.

To attach the pacemaker 602 to the delivery catheter, as shown in FIG. 6A, the distal feature 626a of tether 622 can be threaded through attachment feature 624 of pacemaker 602. Once the tether is threaded through the attachment feature, the tether can be folded back against itself, so that distal feature 626a is adjacent to, but not directly beside proximal feature 626b. The distal and proximal features should be aligned in an un-aligned or "unlocked" configuration, as described above in the two-tether embodiments. This configuration allows the distal and proximal features to be inserted into hole 628 of docking cap 618, as shown in FIG. 6B. Once the distal and proximal features are advanced past the hole 628, an interior chamber (not shown) in the catheter opens up to a diameter larger than the diameter of the hole 628. This interior chamber has a diameter large enough to accommodate both the distal and proximal features in a side by side or "locked" configuration. Thus, the length of the tether can be adjusted to align the distal and proximal features in the side by side configuration, causing the combined cross sectional diameter of the distal and proximal features to be larger than the diameter of hole 628. The result is the locking of tether 622 within the delivery catheter.

Other features of the embodiment of FIGS. 6A-6B can be the same as described above, such as the torque keys, slots, and shafts that allow the delivery catheter to apply rotational torque to the pacemaker to screw it into tissue.

For additional detail regarding the catheter-based delivery systems described above with respect to FIGS. 1D-6B, see U.S. Pat. Nos. 8,615,310, 8,958,892, and 9,205,225. Other catheter-based delivery systems, such as those disclosed in U.S. Patent Applications 62/408,494 and 62/434,537, may also be employed to deliver a leadless pacemaker. Any of these catheter-based delivery systems and associated leadless pacemakers are readily capable of being coupled together in the catheterization laboratory via the loading tool and associated methods discussed in the following section of the present disclosure.

b. Locking Hub with Movable Lumen Segment and Associated Method of Use

Figure 7A:
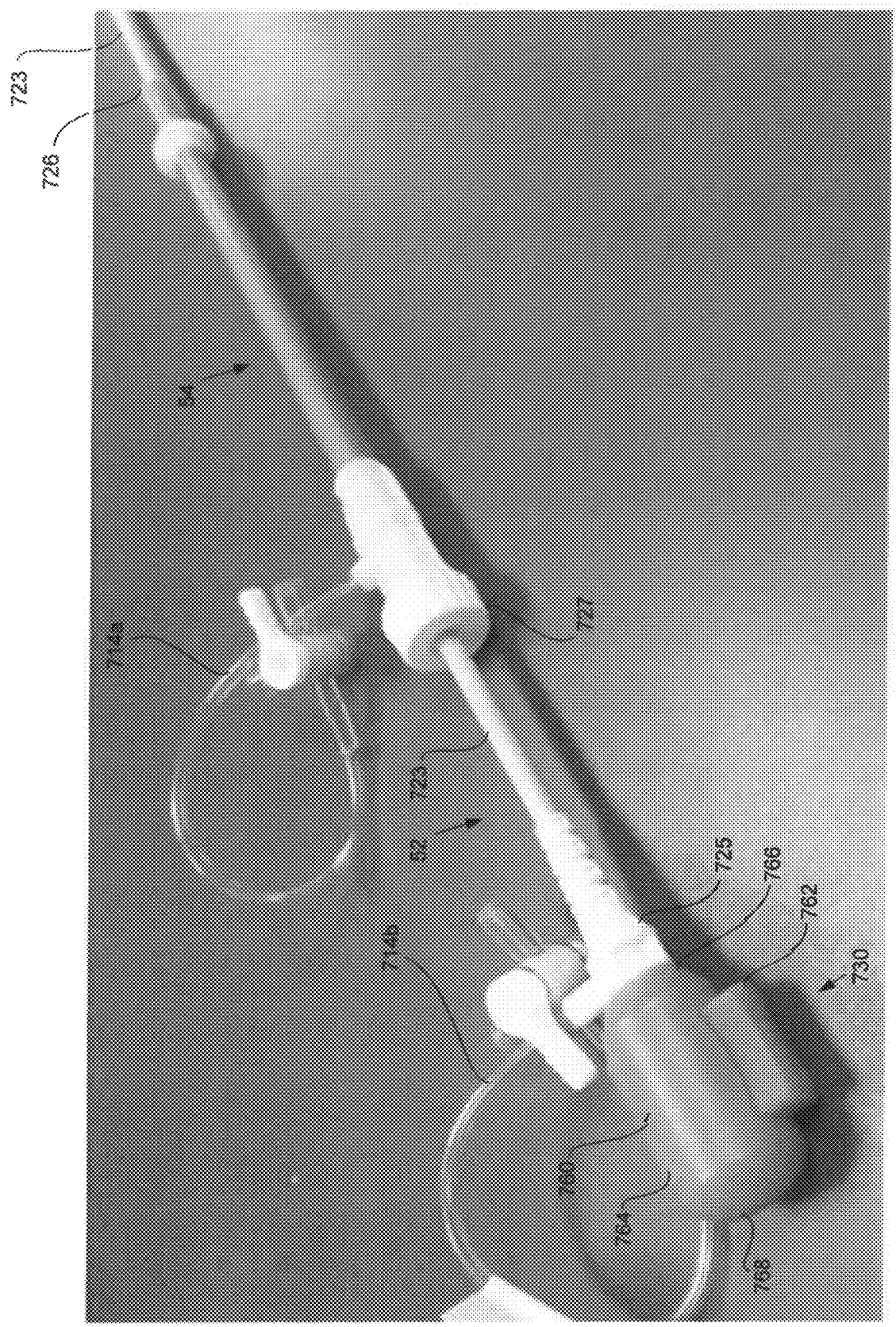
FIG. 7A is an isometric view of a proximal end of the guide catheter extending through the introducer sheath.

FIG. 7A is an isometric view of a proximal end of the guide catheter 52 extending through the introducer sheath 54. As can be understood from FIG. 7A, the locking hub 730 proximally extends from the proximal hub 725 of the guide catheter 52. The locking hub 730 includes a body 760 and a compression button 762 projecting from a lateral side surface 764 of the body. The body also includes a distal end 766 and a proximal end 768 opposite the distal end, the distal end abutting against, and connecting to, the proximal end of the proximal hub 725 of the guide catheter 52.

As discussed in detail below, the compression button 762 has a round or eccentric lumen section 770E through its length that is slightly larger in diameter than the diameter of the shaft 106 of the deflectable catheter 50 that extends through the guide catheter 52 and its locking hub 130, as can be understood from FIG. 1D. On the top side of the lumen section 770E is a hard, low friction material 781, and on the bottom side 782 of the lumen section 770E is a soft, high friction material. When the user is not pushing on the compression button 762, the high friction material on the compression button is in contact with the deflectable shaft, allowing the hub to lock onto the shaft. When the user pushes the compression button into the hub body 760, the locking hub 730 is no longer locked onto the deflectable shaft.

Figure 7B:
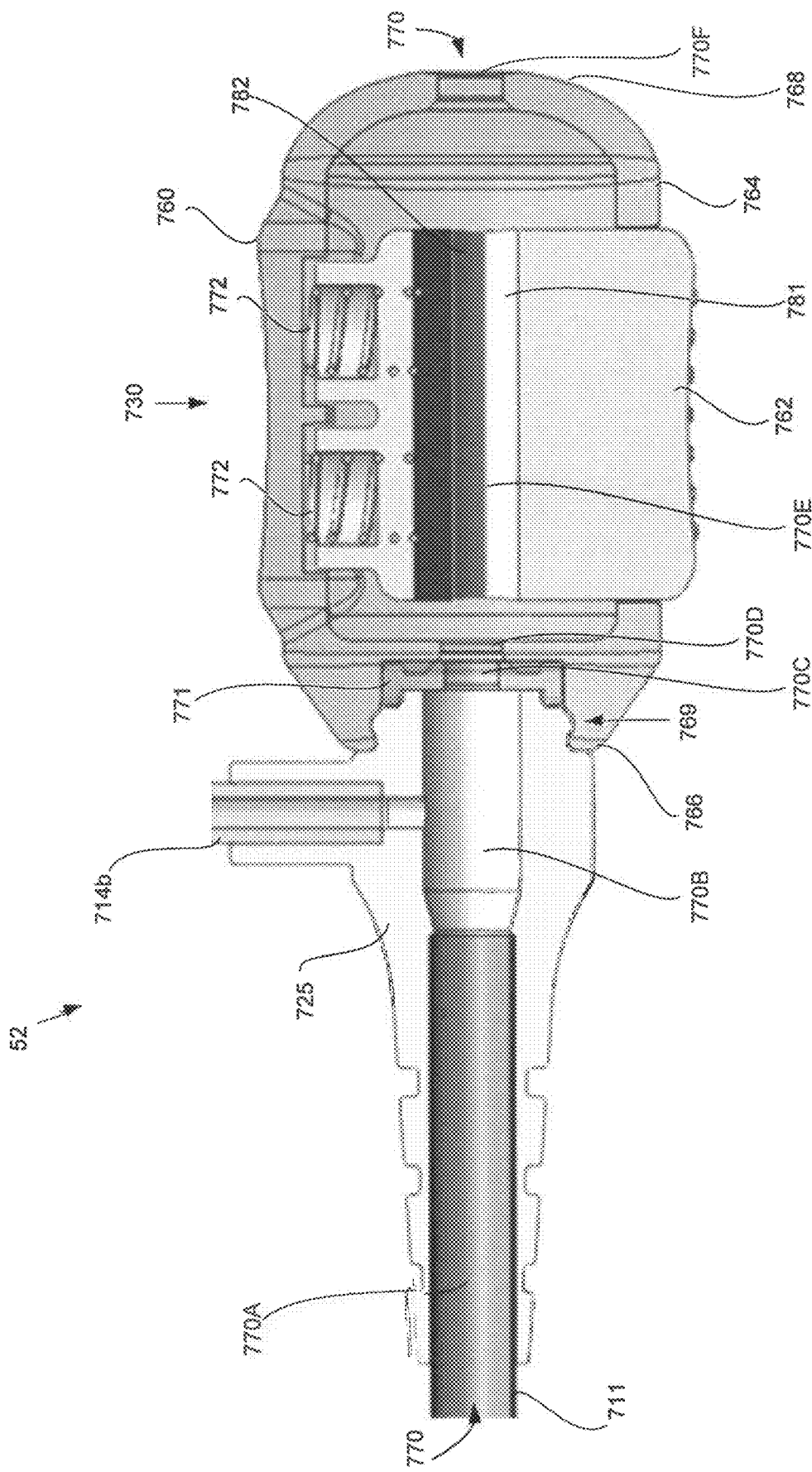
FIG. 7B is a longitudinal cross section of the proximal extent of the guide catheter, including its proximal hub, locking hub and a proximal end of its shaft.

FIG. 7B is a longitudinal cross section of the proximal extent of the guide catheter 52, including its proximal hub 725, locking hub 730 and a proximal end of its shaft 711. As can be understood from FIG. 7B, a male-female interference fit arrangement 769 is formed between a female coupling structure of the distal end 766 that receives a male coupling structure of a proximal end of the proximal hub 725. The interference fit may be sufficient to maintain the locking hub attached to the proximal hub, or the interference fit may be supplemented by being welded or via application of an adhesive. Alternatively, the locking hub 730 to could attached to the proximal hub 725 or another portion of the guide catheter via molding, ultrasonic or other types of welding, or adhesive bonding.

As shown in FIG. 7B, a lumen 770 extends as lumen segments 770A, 770B, 770C, 770D, 770E and 770F through the shaft 711, the proximal hub 725 and components of the locking hub 730, respectively. One component of the locking hub includes an elastomeric seal 771 sandwiched between the opposed surfaces of the male and female coupling structures forming the male-female interference fit arrangement 769. The elastomeric seal 771 includes an opening 770C, which forms one of the lumen segments and is coaxially aligned with the lumen segments 770A, 770B, 770D and 770F. In one embodiment, the elastomeric seal 771 is formed of, without limitation, one or more of silicone rubber, silicone polyurethane copolymer, or other rubber-like polymers and substances.

The opening 770C of the elastomeric seal 771 defines a distal opening into the rest of the lumen 770 extending proximally through the locking hub 730 to proximally daylight at a proximal opening 770F in the body 760. This proximal opening 770F is also coaxially aligned with the lumen segments 770A, 770B, 770C and 770D and defines a proximal opening into the rest of the lumen 770 extending distally through the locking hub 730 and the rest of the guide catheter 52. Immediately proximally adjacent the opening 770C in the elastomeric seal 771 is the distal opening 770D in the body 760, which is coaxially aligned with the lumen segments 770A, 770B, 770C and 770F.

As depicted in FIG. 7B, the compression button 762 occupies a void in the body 760 and includes a lumen segment 770D extending the longitudinal length of the button. Springs 772 act between the button 762 and the body 760 such that the button projects from the side 764 of the body and the lumen segment 770D of the button is out of coaxial alignment with the rest of the lumen segments 770A, 770B, 770C and 770E. This out of alignment condition is also reflected in FIG. 7C, which is a longitudinal cross section of the locking hub 730 in the locked state wherein the button of the locking hub is biased to lock the locking hub on the shaft of the deflectable catheter and prevent displacement between the locking hub and the shaft of the deflectable catheter.

Figure 7D:
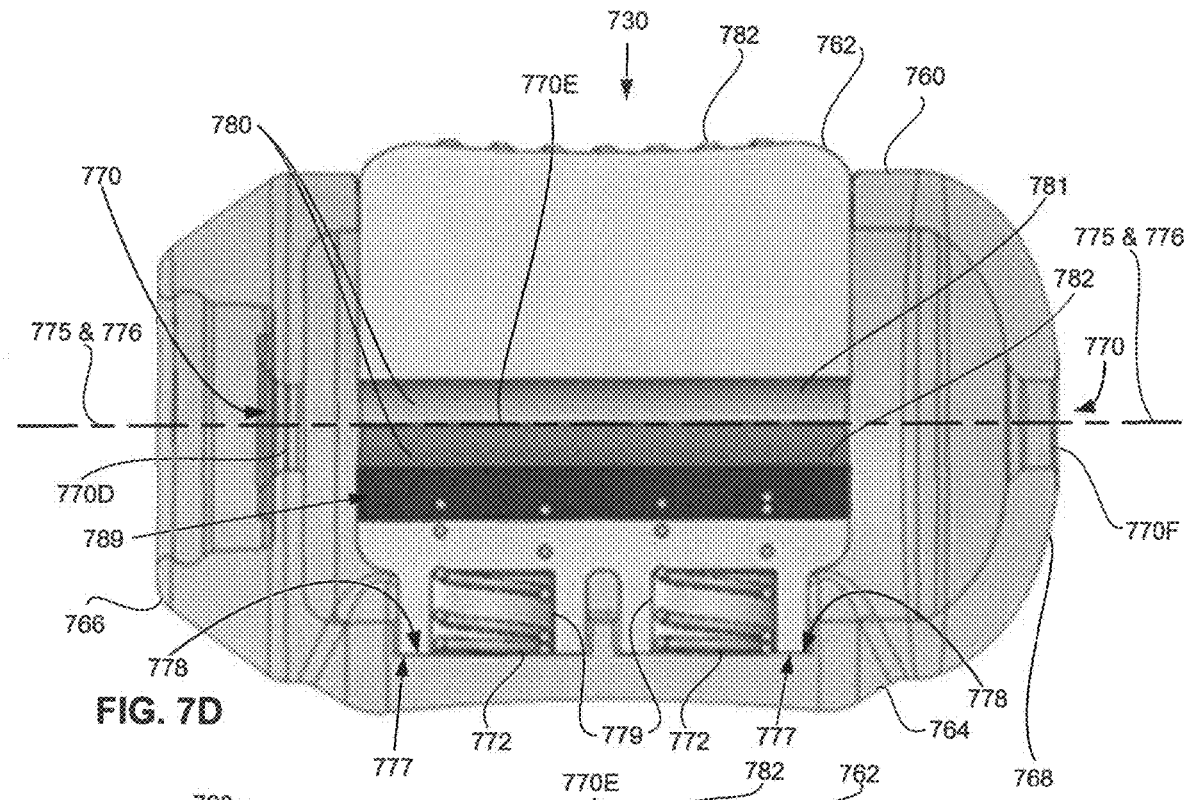
FIG. 7D is the same view as FIG. 7C, except the compression button has be pressed into the body to cause the locking hub to assume an unlocked state whereby the shaft of the deflectable catheter is free to displace relative to the locking hub.
Figure 7C:
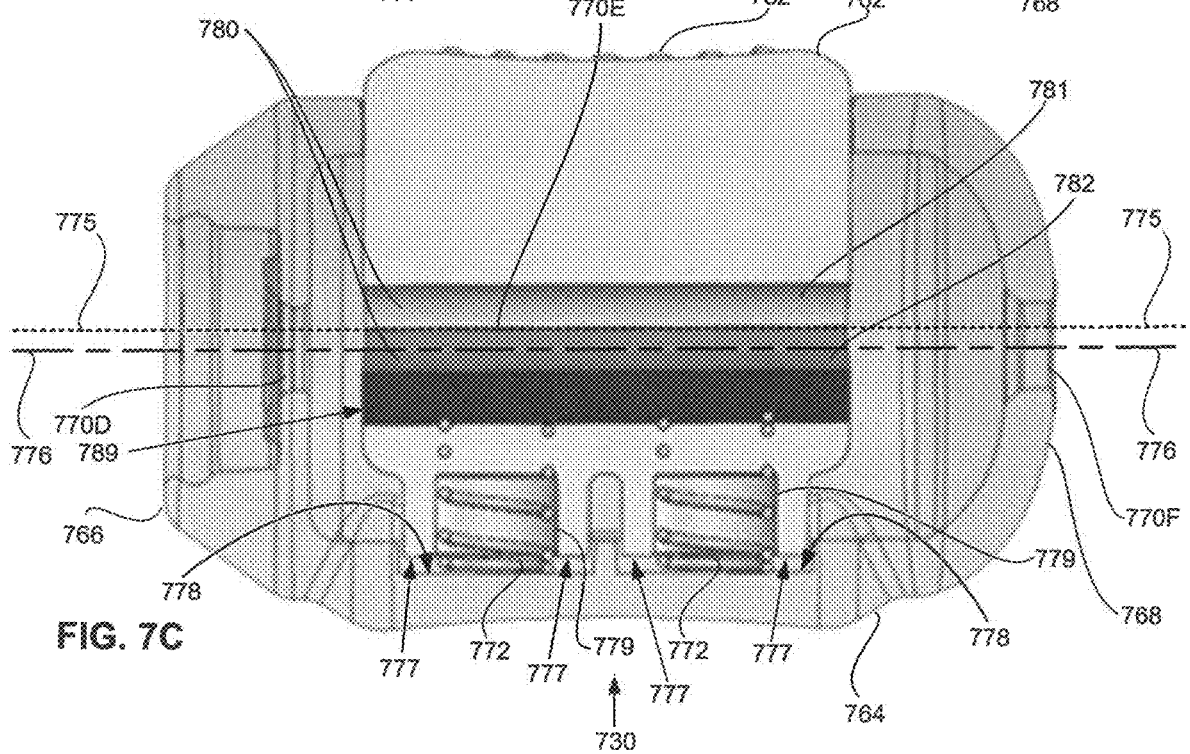
FIG. 7C is a longitudinal cross section of the locking hub in a locked state wherein the button of the locking hub is biased to lock the locking hub on the shaft of the deflectable catheter and prevent displacement between the locking hub and the shaft of the deflectable catheter.

For example, as reflected in FIG. 7C, the springs 772 bias the button 762 outward such that the longitudinal axis 775 of the button lumen 770E is not coaxial (i.e., is out of alignment) with the longitudinal axis 776 of the rest of the lumen segments 770D and 770F (and by extension and as can be understood from FIG. 7B, the lumen segments 770A, 770B and 770C). In such a locked state, a catheter shaft, such as, for example, the shaft 106 of the deflectable catheter 50, is pinched, clamped or compressed by the lumen section 770E of the button being out of alignment with the rest of the lumen sections 770A, 770B, 770C, 770D and 770F forming the overall lumen 770 with the button lumen section 770E. As a result, the locking hub is locked on the catheter shaft 106 and relative displacement between the shaft and locking hub is prevented.

FIG. 7D is the same view as FIG. 7C, except the compression button has be pressed into the body to cause the locking hub to assume an unlocked state whereby the shaft of the deflectable catheter is free to displace relative to the locking hub. Specifically, as illustrated in FIG. 7D, when the button 762 is depressed inwardly against the biasing force of the springs 772 a sufficient distance that an inward limit structure 777 of the button 762 abuts against an inward limit structure 778 of the body 760 (also see FIG. 7C for the limit structures), the longitudinal axes 775, 776 of the lumen segments 770D, 770E and 770F are placed in coaxial alignment. Thus, a catheter shaft 106 extending through the overall lumen 770 is no longer pinched, clamped or compressed by the lumen section 770E of the button and is thereby free to displace through the overall lumen 770.

The limit structures 777 of the compression button 762 may be in the form of the most inward extents or edges 777 of the cylindrical openings 779 that serve as receptacles for the springs 772, as can be understood from FIGS. 7C and 7D. The nature of these cylindrical openings 779 and the inward extents 777 of the button 762 are readily apparent in FIG. 7E, which is an isometric view of the compression button as viewed from its inward side. Specifically, each cylindrical openings 779 and respective inward extent 777 defines a cylindrical protrusion 788, as reflected in FIG. 7E.

Similar cylindrical openings in the interior of the body 760 similarly provide receptacles for the other ends of the springs 772, as can be understood from FIGS. 7C and 7D. Accordingly, for each spring 772, one end of the spring is received in the cylindrical opening 779 of the button, and the opposite end of the spring, plus the surrounding cylindrical protrusion 788 that defines the cylindrical opening 779 of the button, is received in the confines of the respective cylindrical opening of the interior of the body 760 when the button 762 is fully displaced inwardly in the body 760 such that the most inward extent 777 of the protrusion 788 ends up abutting against the inward limit structure 778 of the body, the inward limit structure of the body defining the floor 778 of the surrounding cylindrical opening in the interior of the body.

In other embodiments, the limit structures of the button and body may be other respective structures that abut at a point in the inward displacement of the button such that the longitudinal axes 775, 776 coaxially align as depicted in FIG. 7D and further inward displacement of the button is prevented by the abutment of the respective limit structures. Also, the springs 772 may be retained in position between the button and body via other structures defined in or on the body and button.

The springs 772 may be helical compression springs. In other embodiments, the helical springs may be replaced with other types of springs that act between the button and body, such as, for example, leaf springs. In other embodiments, the springs 772 may be replaced with another type of biasing member that acts between the button and the body, such as, for example, a resilient elastomeric body. The biasing force may also be a biasing arm or other member extending from the button as a part of the unitary construction of the button to act against the body. Of course, such an arrangement could be reversed such that the biasing arm or other member extends from the body as part of the unitary construction of the body to act against the button.

Regardless of what type of biasing mechanism is employed to bias the button outwardly relative to the body and, thereby, cause the lumen axes 775, 776 to be out of alignment as depicted in FIG. 7C, the biasing mechanism can be sized appropriately to provide the proper locking force of the locking hub onto the shaft 106 of the deflectable catheter 50, as can be understood from FIG. 1D.

Figure 7E:
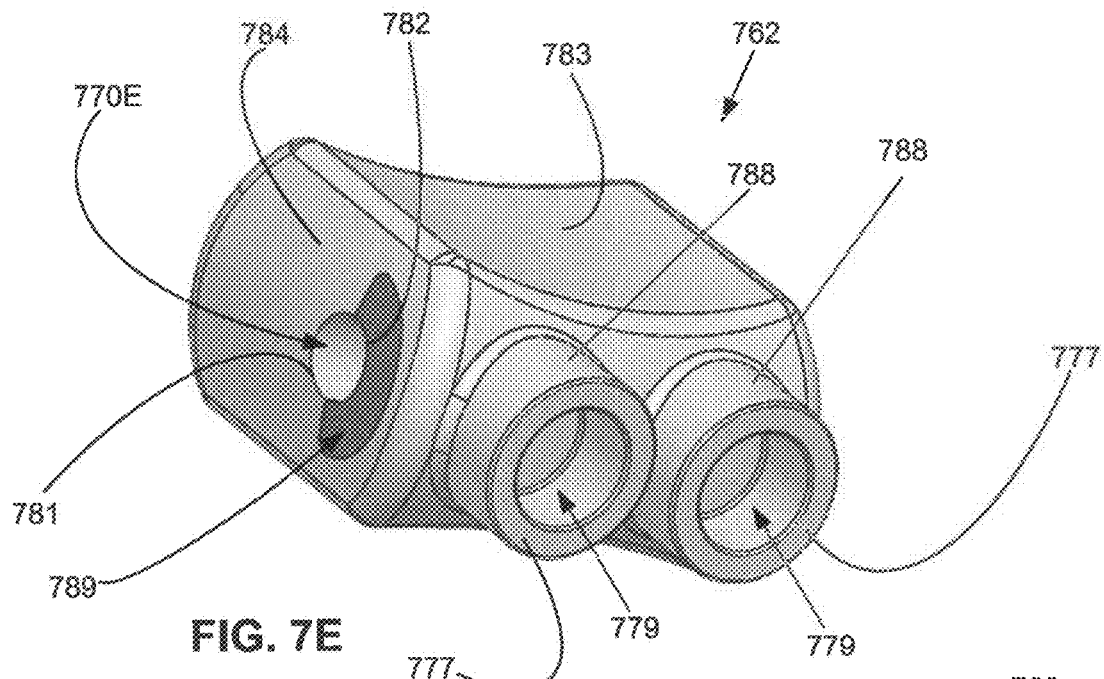
FIG. 7E is an isometric view of the compression button as viewed from its inward side.

As indicated in FIGS. 7C-7E, the cylindrical wall 780 of the lumen section 770E of the compression button 762 may be in the form of an upper semi-cylindrical portion 781 and a lower semi-cylindrical portion 782. The upper portion 780 is adjacent an outer actuation or depression surface 782 of the button 762 that is acted upon by the user when depressing the button. The lower portion 782 is opposite the upper portion 781 and adjacent the inward extents 777 of the button 762. The upper portion 781 may be part of the material of the overall button 762, which, in one embodiment, may be formed of various polymers. Other materials such as ceramic or metal would not be ideal but would not be outside the scope of this invention. In one embodiment, the overall button 762 may be injection molded as a single piece or as two or more pieces and ultrasonically welded, snap fit, or bonded together.

The lower portion 782 may be of another material 789 that is different from the material of the rest of the button 762 and have a surface texture that is more likely to adhere or grip a tubular body extending through the lumen section 770E. In other words, the lower portion 782 may have a higher coefficient of friction than the upper portion 781. In one embodiment, the lower portion 782 may be formed of silicone rubber or a low durometer polymer. The lower portion 782 may be molded, injected, inserted or otherwise provided within the confines of the rest of the button 762 to define the lumen segment 770E in combination with the upper portion 781.

The embodiment depicted in FIG. 7B shows the elastomeric seal 771 and the elastomeric semi-circular lumen portion 782 as being separate elements. However, in other embodiments, the elastomeric seal 771 may be part of the same unitary construction as the elastomeric semi-circular lumen portion 782, the seal 771 and lumen portion 782 being joined together by a flexible elastomeric extension continuously extending uninterrupted between the seal and lumen portion, the lumen portion 782, seal 771 and extension all forming together a unitary body. In such an embodiment, the flexible elastomeric extension is sufficiently flexible to allow for displacement of the button 762 between its non-aligned and aligned states respectively depicted in FIGS. 7C and 7D.

Figure 7F:
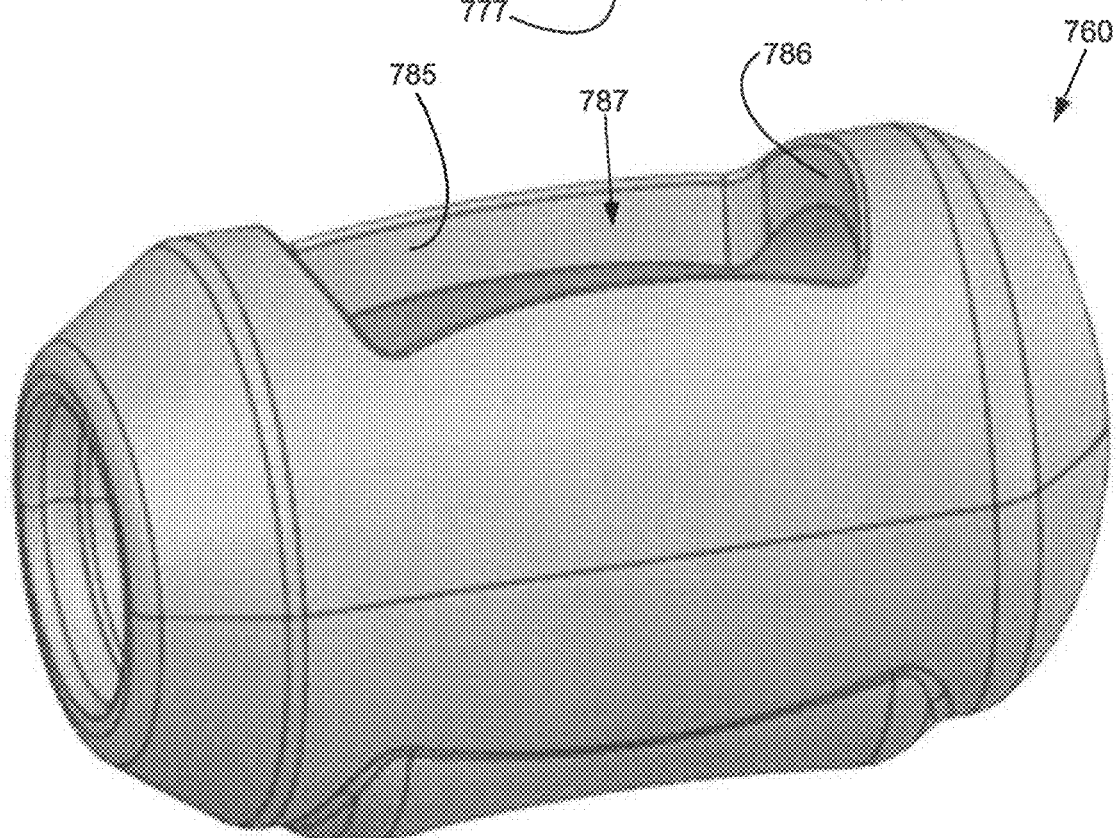
FIG. 7F is an isometric view of the body of the locking hub as viewed from its side.

As indicated in FIG. 7E, the exterior of the compression button 762 includes lateral sidewalls 783 and end sidewalls 784. As can be understood from a comparison of FIG. 7E to FIG. 7F, which is an isometric view of the body 760 of the locking hub as viewed from its side, these sidewalls 783, 784 of the button may have contours that respectively match the sides 785 and ends 786 of the opening 787 that is occupied by the button 762. As a result of the sliding interface formed between the button sidewalls 783, 784 and the sides 785 and ends 786 of the opening 787 of the body 760, the button 762 can displace in a guided and restricted manner only inward and outward within the opening 787, as can be understood from FIGS. 7C and 7D.

As can be understood from FIGS. 7A-7E, in one embodiment, the button 762 includes a contoured surface that provides ergonomic contact for user digit contact. This contoured button surface may be textured or not, and may or may not have a resilient or soft-touch surface to improve grip. This soft-touch surface may be over-molded over the rest of the button.

Similarly, as can be understood from FIGS. 7A-7F, the bottom of the hub body 760 may be ergonomically contoured to help the user maintain grip on the locking hub while sliding the guide catheter 52 relative to the shaft 106 of the deflectable catheter 50, as can be understood from FIG. 1D. This protrusion could have features added to it to or be made of a soft-touch surface to further improve grip. This contoured surface of the body may be textured or not, and may or may not have a resilient or soft-touch surface to improve grip. This soft-touch surface may be over-molded over the rest of the body.

In one embodiment, the body 760 is formed of Arkema Pebax 7233 SA01 or a similar material. In one embodiment, the body may be injection molded as a single piece or as two or more pieces and ultrasonically welded together.

In an example procedure for implanting a leadless pacemaker 102 via the delivery system 100 disclosed herein, the guide catheter 52, with its integrated protective sleeve 104, is advanced and retracted multiple times along the deflectable catheter 50. Depending on the procedural sequence of steps, the guide catheter may be advancing or retracting several centimeters or millimeters.

For example, during introduction of the leadless pacemaker and delivery system into the patient, the guide catheter is fully retracted (e.g., approximately 5 cm) along the deflectable catheter, exposing the leadless pacemaker on the distal end of the deflectable catheter and reducing the overall diameter that must be passed into the patient via the percutaneous access. Once in the femoral vein, the user fully advances the guide catheter over the deflectable catheter to cause the integrated protective sleeve guide catheter to surround the leadless pacemaker to protect the surrounding tissue from trauma. As the system is navigated across the tricuspid valve, the user may find improved performance by subtlety retracting the protective sleeve (e.g., retracting the guide catheter millimeters along the deflectable catheter). When approaching sensitive tissue structures (e.g., the right ventricle apical region or right atrium, or any other friable tissue substrates) of the final implant location, subtle advancements or retractions (e.g., advancing/retracting the guide catheter millimeters along the deflectable catheter) may enhance the device safety and improve implant control.

To facilitate the precisely controlled displacement of the guide catheter 52 relative to deflectable catheter 50 about which the guide catheter extends, the locking hub 130 of the guide catheter may be employed. Specifically, when the button 762 of the locking hub 730 is not actuated to align the longitudinal axis 775 of its lumen section 770E with the longitudinal axis 776 of the rest of the overall lumen 770, the locking hub 730 locks on the shaft 106 of the deflectable catheter 50 as described above, thereby allowing for the locking hub to be grasped to move both the guide catheter 52 and the deflectable catheter 50 together as one unit. On the other hand, when the button 762 of the locking hub 730 is actuated to align the longitudinal axis 775 of its lumen section 770E with the longitudinal axis 776 of the rest of the overall lumen 770, the locking hub 730 no longer locks on the shaft 106 of the deflectable catheter 50, and the locking hub can be grasped to move the guide catheter 52 independent and relative to the deflectable catheter 50, thereby making it possible to cause the leadless pacemaker to recess within or extend from the integrated protective sleeve 104 of the guide catheter 50.

While the locking hub disclosed herein is discussed in the context of allowing a shaft of a deflectable catheter to selectively displace through the locking hub and its guide catheter, in other embodiments, the shaft extending through the locking hub may be another type of elongated body, including for example a guidewire, stylet or another type of catheter or sheath. Also, the locking hub may be employed on other types of delivery systems whether in the context cardiology or elsewhere.

Figure 8:
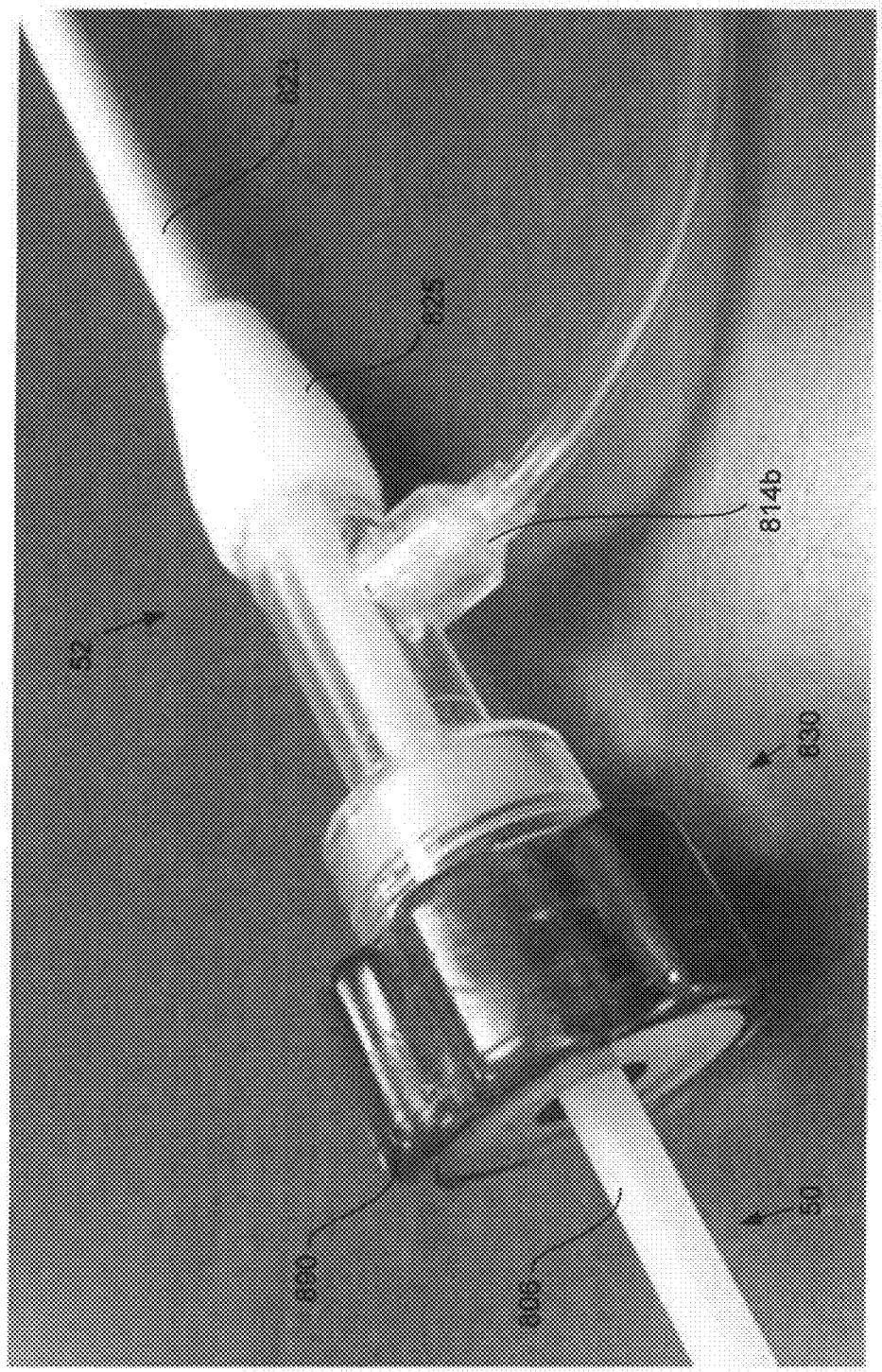
FIG. 8 is an isometric view of a proximal end of the guide catheter with the shaft of the deflectable catheter extending there through, the locking hub employing aspects of a Tuohy-Borst valve.

While the selectable locking concepts discussed herein are given in the context of the above described dual textured lumen section 770E extending through a biased actuation button, similar control and benefits may be obtained by locking hubs employing other locking mechanism such as, for example and without limitation, one or more of mechanical clips similar to clothes pins, hydraulic or electronically actuated clamps, and screw mechanisms. For example, as illustrated in FIG. 8, which is an isometric view of a proximal end of the guide catheter 52 with the shaft 806 of the deflectable catheter 50 extending there through, in one embodiment the locking hub 830 employs aspects of a Tuohy-Borst valve. Specifically, sealing actuation is via clockwise or counter-clockwise torque to a twist hub 890.

One version of the embodiment depicted in FIGS. 7A-7F may be configured for hydraulic or electronic actuation of the lumen section 770E as opposed to displacement caused by user digit pressure.

b. Locking Hub with Longitudinal Biasing Element and Associated Method of Use

The previously discussed implementation of FIGS. 7A-7F generally included a locking hub including a segment of a catheter lumen. The locking hub including biasing elements, such as springs, that biased the lumen segment into misalignment with the rest of the lumen. By doing so, a shaft or similar elongate body disposed within the lumen segment is similarly misaligned or pinched, thereby preventing movement of the elongate body relative to the catheter. By depressing a button (or similar feature) the lumen segment could be brought into coaxial alignment with the rest of the lumen. Accordingly, the previously disclosed implementation generally relied on misalignment or displacement of the lumen segment relative to the rest of the lumen in order to provide pinching or locking functionality for preventing movement of an elongate body disposed within the catheter.

In other implementations, the diameter of the lumen segment may instead be varied to selectively restrict movement of the elongate body within the catheter. As described below in more detail, one such implementation includes a locking hub having a compressible seal element shaped to be disposed about an elongate body extending through the catheter. The locking hub is biased such that a force is applied to the seal element, compressing the seal element and reducing the diameter of the lumen segment. Such reduction in the diameter of the lumen segment causes the seal to frictionally engage the elongate body, thereby resisting or preventing movement of the elongate body relative to the catheter. In other words, the locking hub is biased to lock or otherwise prevent movement of the elongate body by compressing the seal element about the elongate body resulting in frictional engagement between the seal element and the elongate body.

The locking hub may be actuated, such as by depressing one or more buttons of the locking hub, to overcome the bias and to allow the seal element to decompress. Such decompression generally expands the seal element, increasing the diameter of the lumen segment and reducing the frictional engagement between the seal element and the elongate body. As a result, the elongate body is allowed to move relative to the locking hub with no or reduced resistance as compared to when the locking hub is in the non-actuated/biased state.

The foregoing implementation may be used, for example, to lock a protective sleeve or sheath about an implantable medical device, such as a leadless pacemaker, during delivery of the implantable medical device into a patient. When delivered, the physician may actuate the locking hub to enable retraction of the protective sleeve, thereby exposing the implantable medical device for implantation. For example, implantable medical devices may include fixation mechanisms (such as a fixation helix) or other features that may become inadvertently caught or otherwise cause damage to patient tissue during their delivery. Accordingly, implementations of the present disclosure ensure that such features of the implantable medical devices are protected during delivery while enabling their ready exposure when implantation is to occur.

Another advantage of implementations disclosed herein is that the locking hub may be used to allow for correct positioning of a protective sleeve or sheath relative to the implantable medical device prior to insertion into the patient. More specifically, a physician may select a sheath for use with a delivery catheter system and, using the locking hub, may adjust the position of the sheath relative to an implantable medical device coupled to a distal end of the delivery catheter system. Once properly adjusted, the sheath may be locked in place. As a result, a single length of sheath may be used in multiple applications and with implantable medical devices of varying dimensions.

Figure 9A:
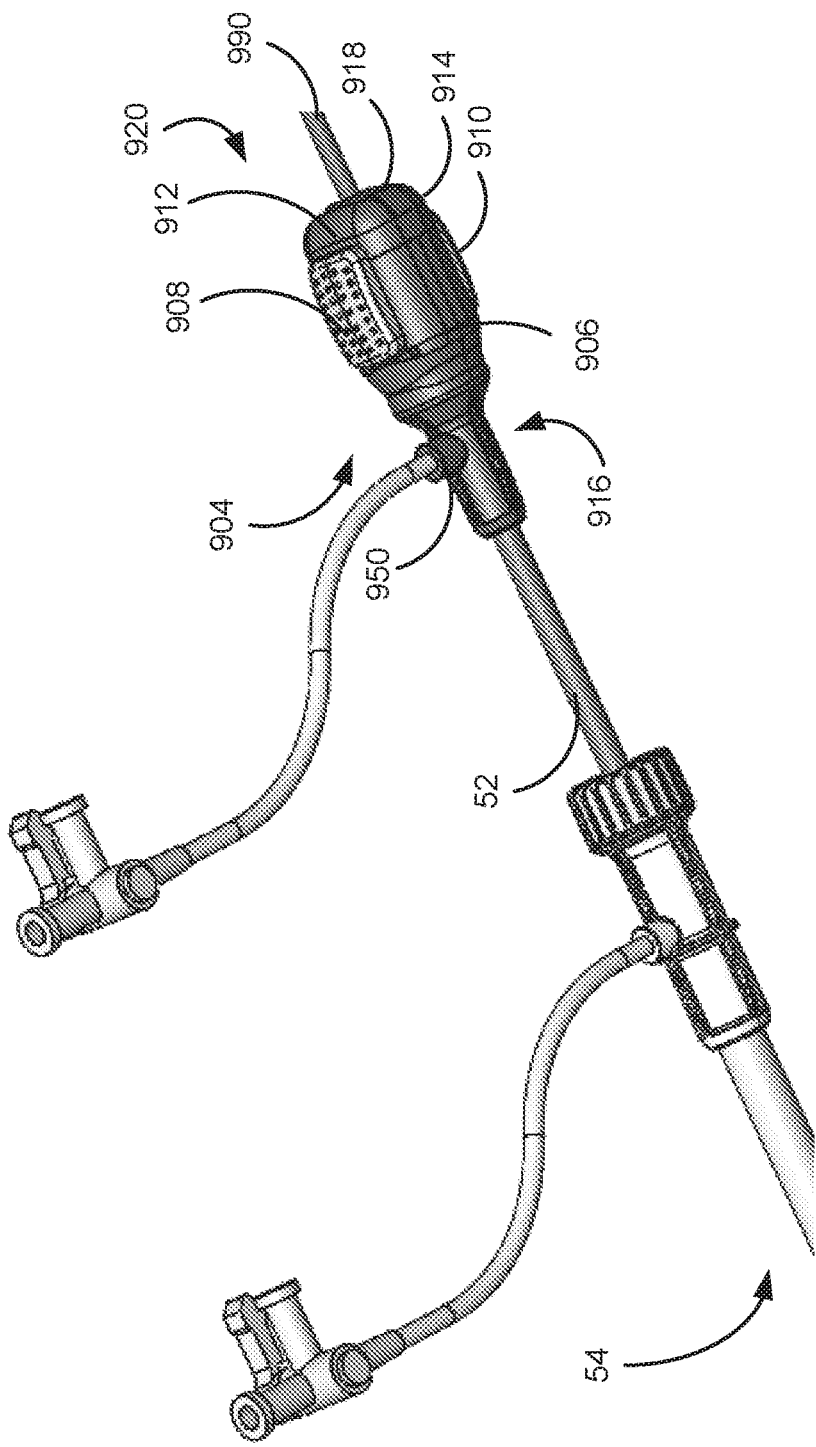
FIG. 9A is an isometric view of a proximal end of a guide catheter including a second locking hub.
Figure 9B:
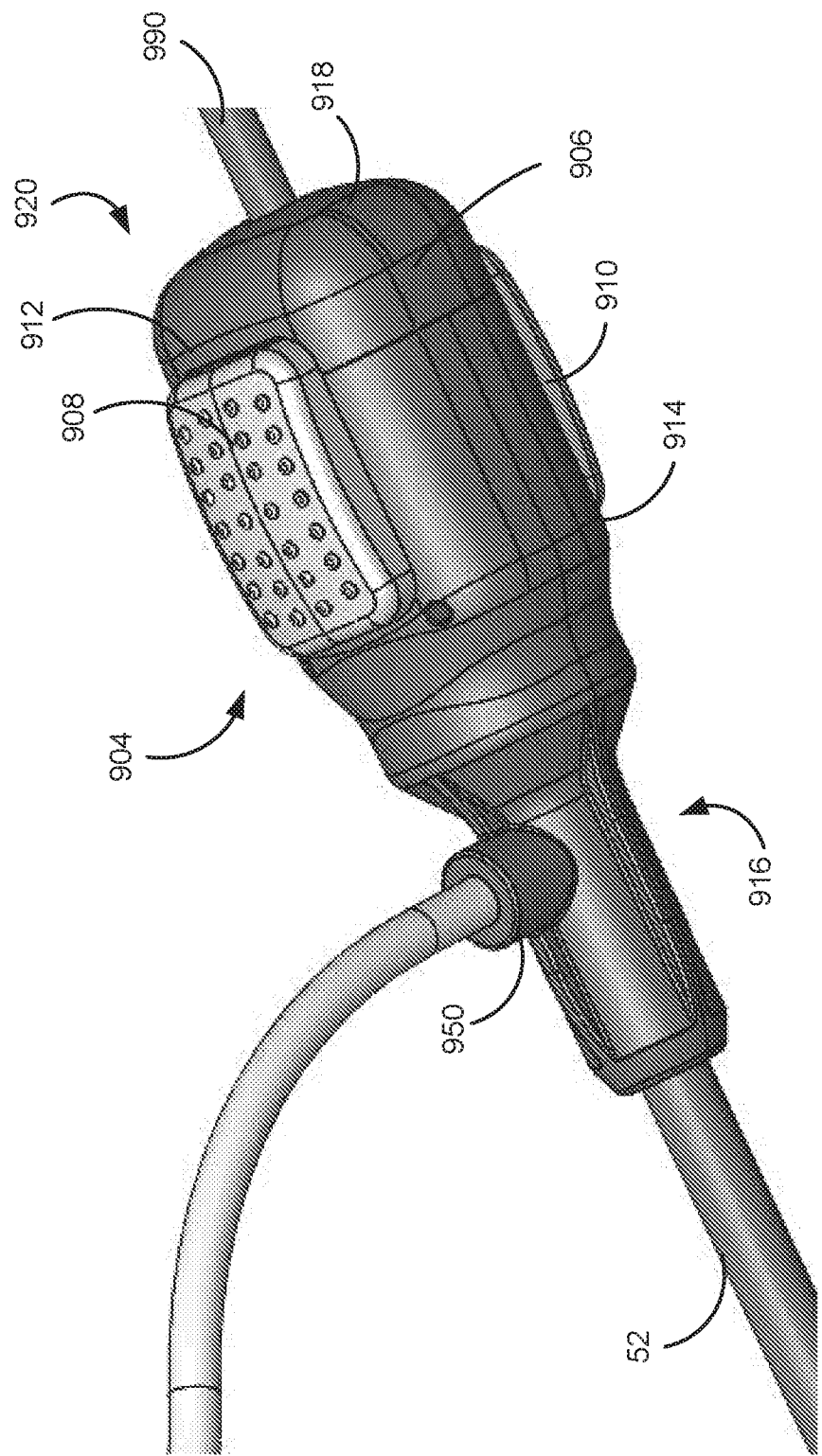
FIG. 9B is a second isometric view of the proximal end of the guide catheter of FIG. 9A.

FIG. 9A is an isometric view of a proximal end of a guide catheter 52 extending through an introducer sheath 54 including an alternative implementation of a locking hub 904. FIG. 9B is a more detailed isometric view of the locking hub 904. As illustrated in FIGS. 9A-9B, an elongate member 990, such as a catheter shaft, may extend through the guide catheter 52 and the locking hub 904. The locking hub 904 includes a body 906 and a pair of compression buttons 908, 910 projecting from opposite lateral side surfaces 912, 914 of the body 906. The body 906 also includes a distal end 916 and a proximal end 920 opposite the distal end 916 and may further include a cap 918 coupled to the proximal end 920. As illustrated, in certain implementations the locking hub 904 may include one or more flush ports, such as flush port 950.

Figure 9C:
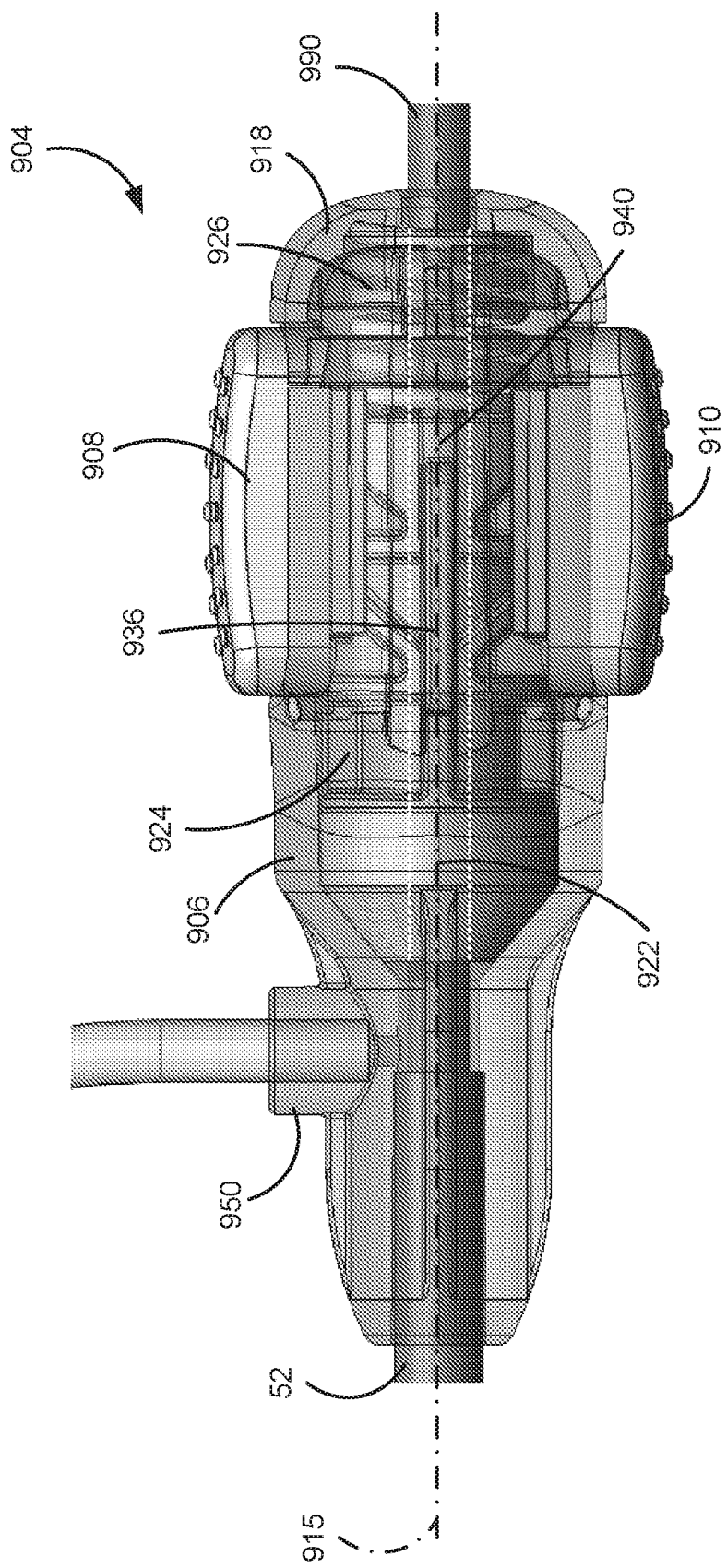
FIG. 9C is an exploded view of the locking hub of FIGS. 9A-9B.
Figure 9D:
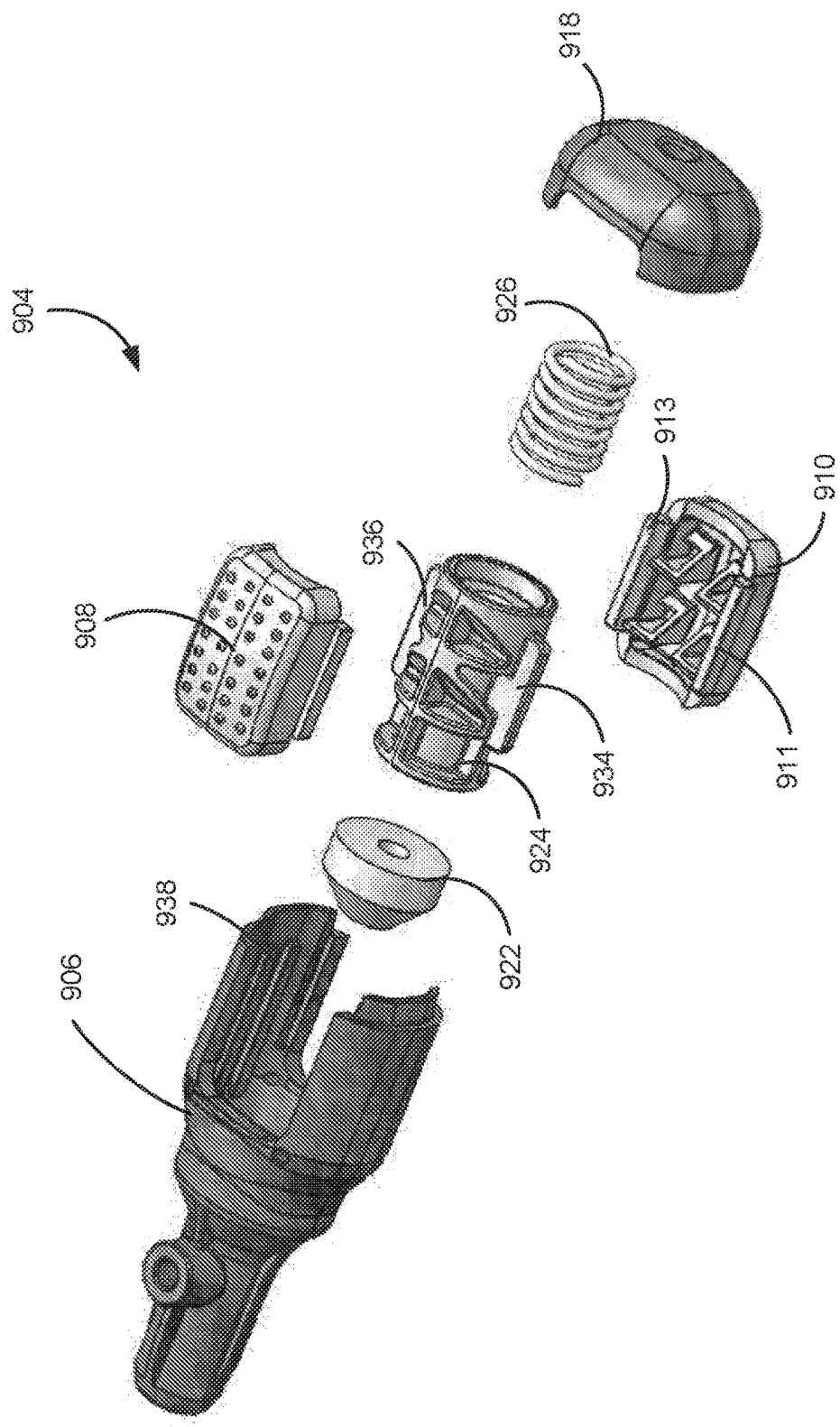
FIG. 9D is a semi-transparent side view of the guide catheter of FIG. 9A-9B including the locking hub.

FIG. 9C is an exploded view of the locking hub 904 and FIG. 9D is a semi-transparent side elevation view of the locking hub 904, each of which are intended to illustrate the internal components and assembly of the locking hub 904.

Referring first to FIG. 9C, the locking hub 904 includes a hub body 906 within which a seal 922, a shuttle 924, and a biasing element 926 are disposed. In the illustrated implementation, the shuttle 924 is disposed proximal the seal 922 and distal the biasing element 926. Each of the seal 922, the shuttle 924, the biasing element 926, and the cap 918 define respective through-bores, thereby allowing insertion of an elongate body 990, such as a deflectable catheter shaft, through the locking hub 904, as illustrated in FIG. 9C.

As illustrated in FIG. 9C, the shuttle 924 may include a plurality of ribs, such as ribs 934, 936, shaped to be received within corresponding channels 938, 940 (channel 940 being shown in FIG. 9D) formed within the hub body 906. When assembled, the ribs 934, 936 are disposed within the channels 938, 940, respectively, such that the shuttle 922 is allowed to translate longitudinally within the hub body 906.

As previously noted, the locking hub 904 further includes buttons 908, 910 that may be used to actuate the locking hub 904, as discussed in more detail below in the context of FIGS. 10A-10B. The buttons 908, 910 may be disposed on lateral sides of the locking hub 904 such that depression of the buttons 908, 910 causes the buttons 908, 910 to translate inwardly toward a longitudinal axis 915 of the guide catheter 52. In certain implementations, each button 908, 910 may include flexible side tabs, such as side tabs 911, 913 of the button 910 (shown in FIG. 9D), that are configured to flex inwardly toward each other to allow insertion of the buttons into the hub body 906. Once inserted the side tabs expand such that they engage the hub body 906, thereby retaining the buttons 908, 910 within the hub body 906.

The biasing element 926 is generally adapted to provide a longitudinal force that biases the shuttle 924 against the seal 922. As illustrated in FIGS. 9C and 9D, for example, the biasing element 926 is a helical spring. In other implementations, however, the helical spring may be replaced or used in conjunction with other similar elements including, without limitation, one or more of a leaf spring, a biasing arm, or a resilient elastomeric member similarly configured to bias the shuttle 924 against the seal 922.

Figure 10A:
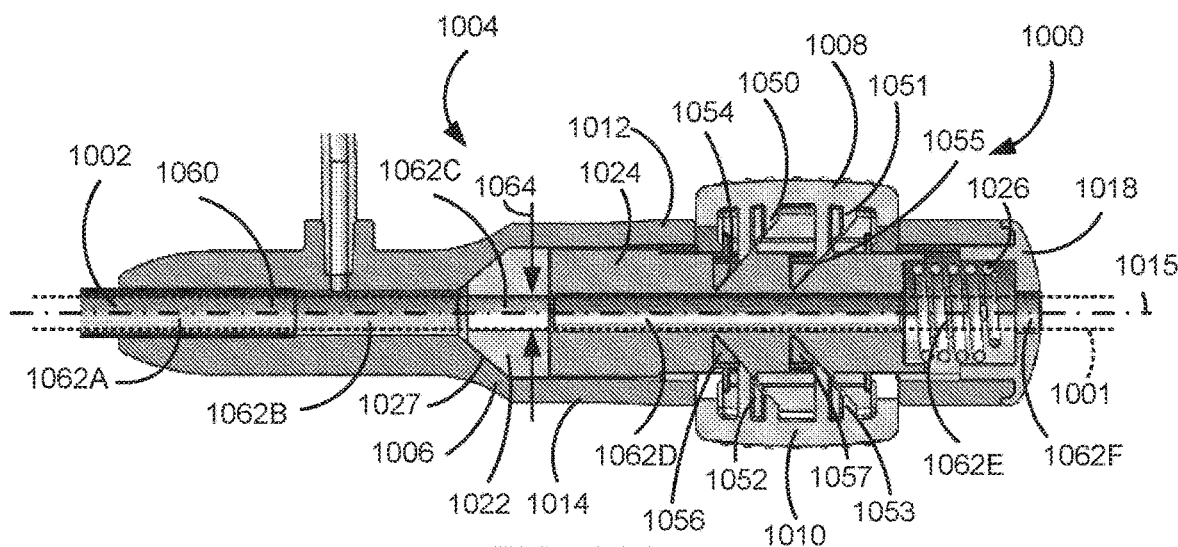
FIG. 10A is a longitudinal cross section of another guide catheter including a third locking hub, the locking hub in a biased/locked configuration.
Figure 10B:
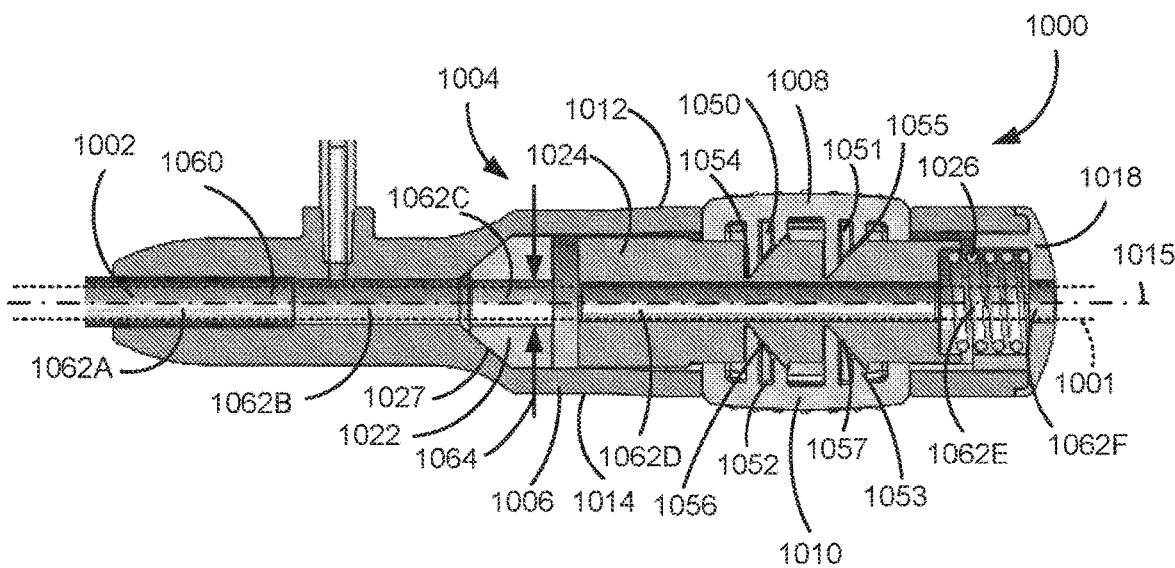
FIG. 10B is a longitudinal cross section of the guide catheter and locking hub of FIG. 10A in an unlocked configuration.

FIGS. 10A-10B are longitudinal cross-sectional views of a catheter 1000 including a guide catheter 1002 having a locking hub 1004. The locking hub 1004 includes a hub body 1006 and a pair of compression buttons 1008, 1010 projecting from opposite lateral side surfaces 1012, 1014 of the hub body 1006. The hub body 1006 also includes a cap 1018. The locking hub 1004 further includes a seal 1022, a shuttle 1024, and a biasing element 1026, each of which is disposed within the hub body 1006.

The guide catheter 1002 and the locking hub 1004 collectively define a lumen 1060 within which an elongate body 1001, such as a shaft, may be disposed. The lumen 1060 may be divided into multiple lumen segments. For example, in the catheter 1000 illustrated in FIGS. 10A-10B, the lumen 1060 may include each of lumen segments 1062A-1062F with lumen segment 1062A being defined by the guide catheter 1002, lumen segment 1062B being defined by a section of the hub body 1006 between the guide catheter 1002 and the seal 1022, lumen segment 1062C defined by the seal 1022, lumen segment 1062D defined by the shuttle 1024, lumen segment 1062E defined by the biasing element 1026, and lumen segment 1062F defined by and extending through the cap 1018.

Each of the lumen segments 1062A-1062F is sized and shaped to receive respective portions of the elongate body 1001 such that the elongate body 1001 extends through the locking hub 1004. The lumen segment 1062C of the seal 1022, however, is further adapted to have a variable diameter. In particular, the seal 1022 is formed of a compressible material such that when the seal 1022 is compressed and a portion of the elongate body 1001 is disposed within the lumen segment 1062C, a diameter 1064 of the lumen segment 1062C is reduced, resulting in frictional engagement of the seal 1022 with the elongate body 1001.

As illustrated in FIG. 10A, the locking hub 1004 is configured to be biased into a locked configuration by disposing the biasing element 1026 proximal the shuttle 1024 such that the shuttle 1024 applies a distal longitudinal force onto the seal 1022, thereby compressing the seal 1022 distally into or against the hub body 1006. In particular, the seal 1022 includes a distal tapered section 1023 that interfaces with a corresponding internal distal tapered surface 1027 of the hub body 1006 such that the longitudinal force applied by the shuttle 1024 is at least partially redirected toward a longitudinal axis 1015 of the catheter 1000. By doing so, the diameter 1064 of the lumen segment 1062C is similarly reduced, thereby causing engagement of the seal 1022 with the elongate body 1001. As a result of this engagement, the elongate body 1001 is locked in place or otherwise prevented from movement relative to the locking hub 1004.

As illustrated in FIG. 10B, the buttons 1008, 1010 may be depressed to transition the locking hub 1004 from the biased/locked configuration into an unlocked configuration in which the elongate body 1001 may be moved relative to the locking hub 1004. More specifically, sufficiently depressing the buttons 1008, 1010 overcomes the longitudinal force provided by the biasing element 1026, causing compression of the biasing element 1026 by proximal translation of the shuttle 1024. As the shuttle 1024 proximally translates, the longitudinal force applied to the seal 1022 by the shuttle 1024 is relieved, allowing the seal 1022 to decompress. Such decompression results in expansion of the diameter 1064 of the lumen segment 1062C such that the seal 1022 no longer frictionally engages the elongate member 1001.

In the implementation illustrated in FIG. 10B, translation of the shuttle 1024 is achieved by interaction between the buttons 1008, 1010 and the shuttle 1024. In particular, each of the buttons 1008, 1010 includes a plurality of angled protrusions, such as protrusions 1050, 1051, 1052, and 1053 that are distally slanted. The shuttle 1024 includes corresponding indentations, such as indentations 1054, 1055, 1056, 1057, shaped to receive each of the angled protrusions when the buttons 1008, 1010 are depressed. As the buttons 1008, 1010 are depressed inwardly, the protrusions push against the indentations and, by virtue of their respective slanted faces, translates the transverse force applied to the buttons 1008, 1010 into a longitudinal force that proximally translates the shuttle 1024.

Figure 11:
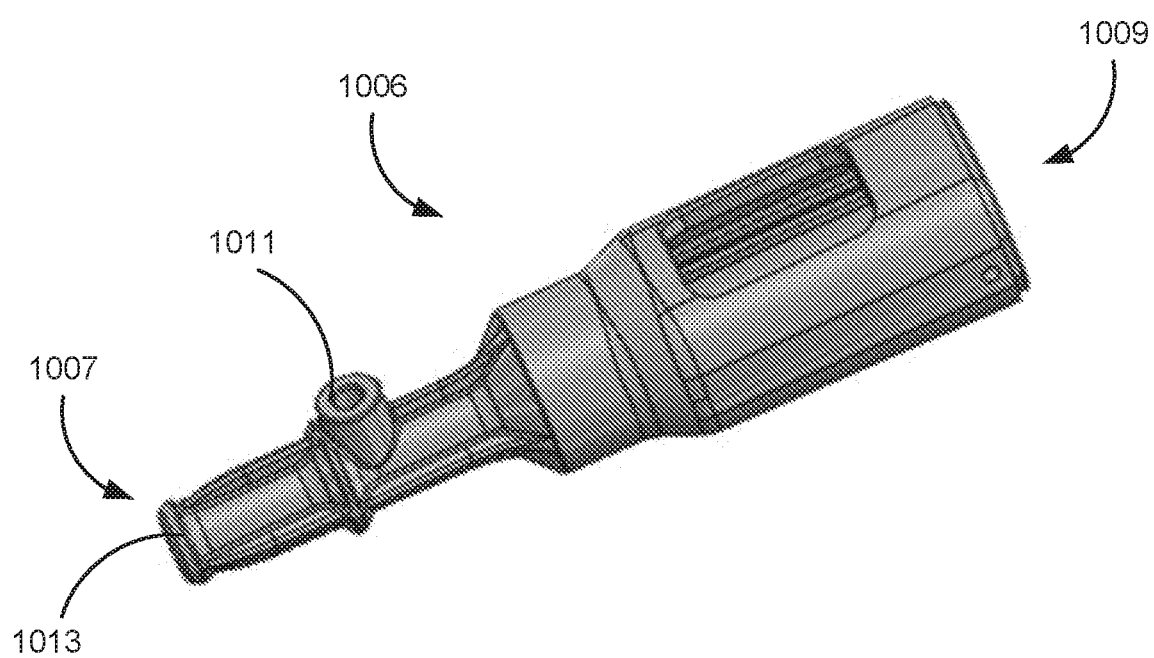
FIG. 11 is an isometric view of a hub body of the locking hub of FIGS. 10A-10B.

FIG. 11 is an isometric view of the hub body 1006 of FIGS. 10A-10B. The hub body 1006 may include a distal end 1007 and a proximal end 1009 opposite the distal end 1007. The distal end 1007 of the hub body 1006 may include a sideport 1011 to facilitate flushing of the hub body 1006. The distal end 1007 includes a distal opening 1013 adapted to receive and be coupled to a proximal end of the guide catheter 1002 (shown in FIGS. 10A-10B). For example, in certain implementations the hub body 1006 is molded or adhesively bonded on the guide catheter 1002.

Figure 12:
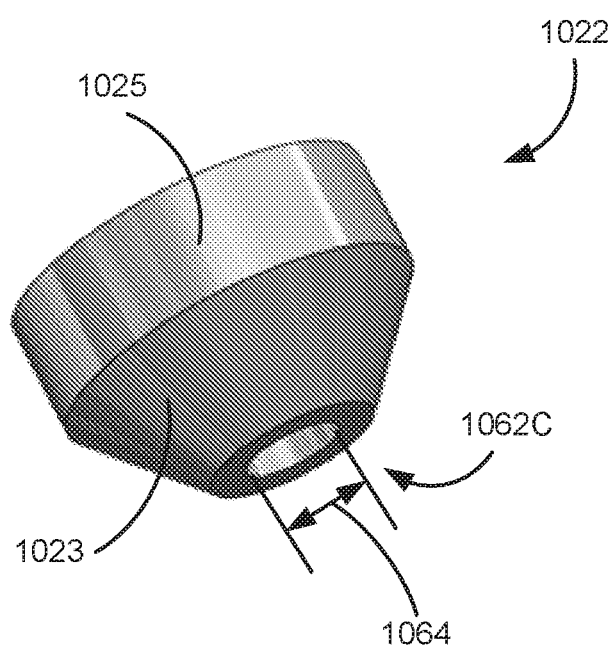
FIG. 12 is an isometric view of a seal of the locking hub of FIGS. 10A-10B.

FIG. 12 is an isometric view of the seal 1022 of FIGS. 10A-10B. As previously discussed, the seal 1022 defines a lumen segment 1062C having an inner diameter 1064. The seal 1022 is sized and shaped such that the diameter 1064 is slightly larger than an outer diameter of the elongate body 1001 (shown in FIGS. 10A-10B) with which the locking hub 1004 is to be used. Accordingly, when in an uncompressed state, the seal 1022 allows free or relatively low friction movement of the elongate body 1001 within the lumen segment 1062C.

As illustrated in FIG. 12, the seal 1022 may include a distal tapered section 1023 and a proximal cylindrical section 1025. As previously noted, the distal tapered section 1023 may be sized and shaped to be received by a corresponding internal tapered surface 1027 of the hub body 1006 (shown in FIGS. 10A-10B) such that when a longitudinal force is applied to the seal 1022, the interface between the distal tapered section 1023 and the internal tapered surface 1027 redirects a portion of the longitudinal force inwardly toward a longitudinal axis 1015 of the catheter 1000 (each illustrated in FIGS. 10A-10B). Such inward force causes reduction of the inner diameter 1064 such that the seal 1022 engages the elongate body 1001. The proximal cylinder section 1025, in contrast, may be sized to be received within a corresponding section of the hub body 1006 proximal the internal tapered surface 1027. In certain implementations, the proximal cylinder section 1025 may be sized to have an outer diameter greater than the inner diameter of the hub body 1006 such that the seal 1022 is maintained within the hub body 1006 by an interference fit.

Figure 13:
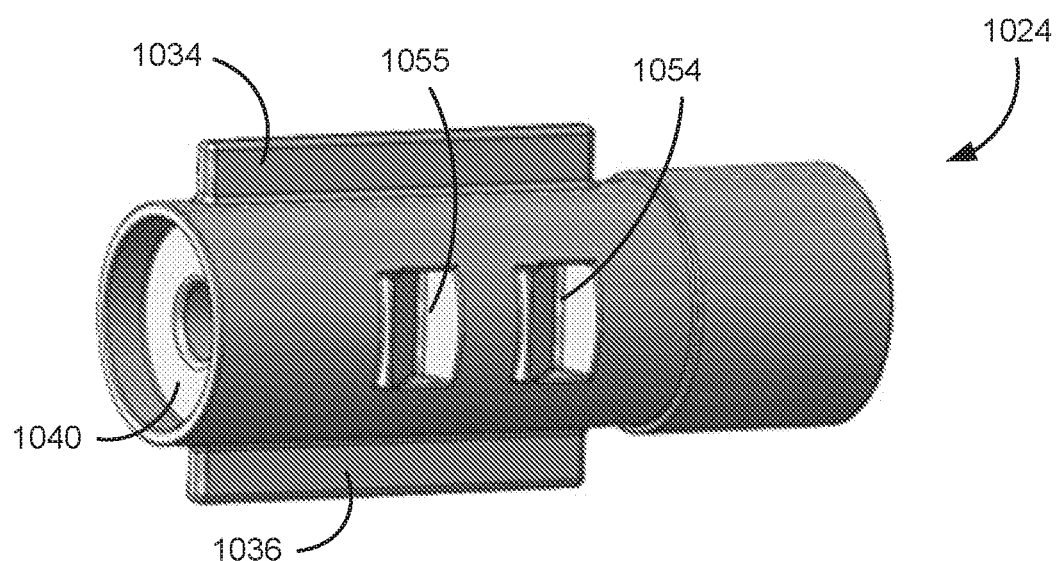
FIG. 13 is an isometric view of a shuttle of the locking hub of FIGS. 10A-10B.
Figure 14:
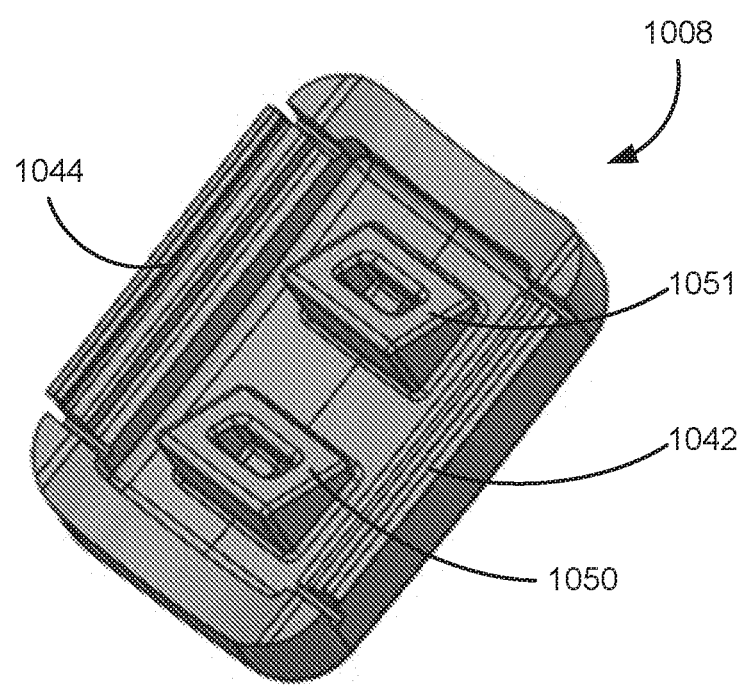
FIG. 14 is an isometric view of a button of the locking hub of FIGS. 10A-10B.

FIG. 13 is an isometric view of the shuttle 1024 of FIGS. 10A-10B. As illustrated, the shuttle 1024 includes indentations disposed on opposite sides of the shuttle 1022. For example, the shuttle 1024 includes indentations 1054, 1055 (indentations 1056, 1057 being disposed on an opposite side of the shuttle 1024, as shown in FIGS. 10A-10B) that receive corresponding angled extensions 1050-1053 of the buttons 1008, 1010. FIG. 14 is an isometric view of the button 1008, for example, further illustrating angled extensions 1050, 1051. As previously discussed in the context of FIGS. 10A-10B, the angled protrusions 1050-1053 of the buttons 1008, 1010 interface with the indentations 1054-1056 of the shuttle 1022 such that when the buttons 1008, 1010 are depressed, the angled protrusions 1050-1053 push against the indentations 1054-1056 to proximally translate the shuttle 1024 within the housing body 1006 and away from the seal 1022. In certain implementations, one or both of the angled protrusions 1050-1053 and the indentations 1054-1056 may be formed from a low friction material or may be coated with a low-friction coating to reduce drag therebetween. The shuttle 1024 is also illustrated as including ribs 1034, 1036 that may be receive by corresponding channels defined by the hub body 1006 to guide the shuttle 1024 within the hub body 1006. The shuttle 1024 may further include a proximal recess 1040 shaped to receive the biasing element 1026.

As previously noted, FIG. 14 is an isometric view of the button 1008 of FIGS. 10A-10B. As illustrated, the button 1008 may include flexible sidewalls 1042, 1044 including lips or similar features shaped to engage the hub body 1006. For example, during assembly the flexible sidewalls 1042, 1044 may be depressed toward each other to allow insertion into the hub body 1006. Once inserted the flexible sidewalls 1042, 1044 may expand such that the lips prevent or resist removal of the button 1008 once inserted into the hub body 1006.

Figure 15:
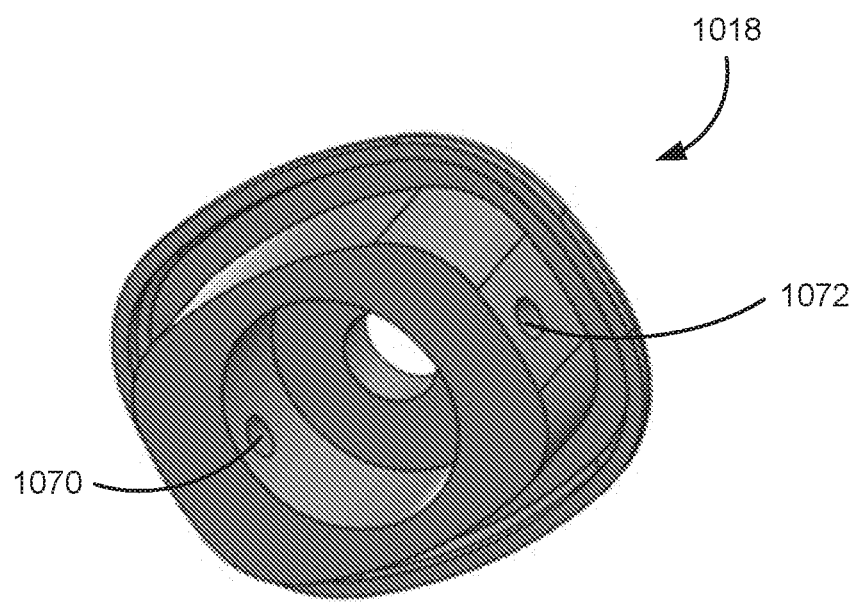
FIG. 15 is an isometric view of a distal cap of the locking hub of FIGS. 10A-10B.

FIG. 15 is an isometric view of the cap 1018 of FIGS. 10A-10B. As previously discussed, the cap 1018 is inserted into and coupled to the proximal end of the hub body 1006. By doing so, the cap 1018 contains the biasing element 1026 and provides a rigid structure against which the biasing element 1026 is supported. In certain implementations, the cap 1018 is coupled to the hub body 1006 by, without limitation, one or more of ultrasonic welding, a snap fit, and an adhesive. Coupling of the cap 1018 to the hub body 1006 may also be reinforced by inserting pins or similar fastening elements through the cap 1018 and into the hub body 1006. For example, the cap 1018 includes holes 1070, 1072 that may be aligned with corresponding holes of the hub body 1006 to receive coupling pins or similar fasteners.

The implementations of the present disclosure discussed in FIGS. 9A-10B include configurations in which the internal components of the locking hub are arranged such that the seal is distally disposed relative to the shuttle and biasing element. In such implementations, the biasing element is configured to bias the shuttle in a distal direction to compress the seal. In other implementations, however, the seal may instead be proximal the shuttle and the biasing element may be distal the shuttle such that the shuttle is biased in a proximal direction against the seal. In such implementations, the seal may be arranged such that it tapers in a proximal direction and the cap of the locking hub may include a tapered internal surface, similar to the internal surface 1027 of the hub body 1006, adapted to cause inward compression of the seal when a longitudinal force is applied to the seal.

Any of the above mentioned embodiments may also include, but are not limited to, electronic indicators on the system (e.g., LEDS or screens) or on adjunct support-screens to communicate status. Finally, the above mentioned embodiments may also include shaft position indicators via, for example, detents located on the shaft of the deflectable catheter and complementary features for interacting on the detents, the complementary features being located on the guide catheter or even the locking hub. Of course the opposite arrangement is also possible. The position indicator aspects can be used to notify the user of the extent to which the protective sleeve covers the leadless pacemaker.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. A delivery system for delivering a leadless pacemaker, the delivery system comprising:
    a catheter including a distal end, a proximal end opposite the distal end, a lumen extending between the distal end and the proximal end, and a locking hub operably coupled to the proximal end, the locking hub comprising a seal element including a lumen segment of the lumen,
    wherein self-biasing of the locking hub compresses the seal element, thereby reducing a diameter of the lumen segment, and
    wherein actuation of the locking hub reduces the compression of the seal element thereby expanding the diameter of the lumen segment.

2. The delivery system of claim 1, wherein the locking hub comprises a movable shuttle and the self-biasing of the locking hub biases the shuttle in a first direction to compress the seal element, the first direction being along a longitudinal axis of the catheter.

3. The delivery system of claim 2, wherein actuation of the locking hub translates the shuttle in a second direction opposite the first direction.

4. The delivery system of claim 2, wherein the locking hub further comprises a biasing element configured to bias the shuttle in the first direction, the biasing element comprising at least one of a helical spring, a leaf spring, a biasing arm, or a resilient elastomeric member.

5. The delivery system of claim 1, wherein actuation of the locking hub comprises depressing one or more buttons of the locking hub such that the one or more buttons translate transversely and inward relative to a longitudinal axis of the catheter.

6. The delivery system of claim 1, wherein the locking hub comprises a locking hub body having a tapered inner surface and the seal element comprises a corresponding tapered outer surface.

7. The delivery system of claim 6, wherein the self-biasing applies a longitudinal force to the seal element such that an interface between the tapered inner surface of the locking hub body and the tapered outer surface of the seal element causes transverse compression of the seal element toward a longitudinal axis of the catheter.

* * * * *